(12) United States Patent
Asakura et al.

(10) Patent No.: US 7,842,483 B2
(45) Date of Patent: Nov. 30, 2010

(54) CYTOCHROME C OXIDASE ENZYME COMPLEX

(75) Inventors: Akira Asakura, Fujisawa (JP); Tatsuo Hoshino, Kamakura (JP); Masako Shinjoh, Kamakura (JP)

(73) Assignee: DSM Nutritional Products, Inc., Parsippany, NJ (US)

( * ) Notice: Subject to any disclaimer, the term of this patent is extended or adjusted under 35 U.S.C. 154(b) by 683 days.

(21) Appl. No.: 11/044,853

(22) Filed: Jan. 26, 2005

(65) Prior Publication Data

US 2005/0123989 A1    Jun. 9, 2005

Related U.S. Application Data

(62) Division of application No. 09/712,768, filed on Nov. 14, 2000, now Pat. No. 6,869,785.

(30) Foreign Application Priority Data

Nov. 17, 1999    (EP)    ................... 99122842

(51) Int. Cl.
C12P 7/40 (2006.01)
C12N 15/00 (2006.01)
C12N 9/02 (2006.01)
C12N 1/21 (2006.01)
C07H 21/00 (2006.01)
C07K 14/00 (2006.01)
C12P 21/00 (2006.01)

(52) U.S. Cl. .................... 435/136; 435/189; 435/320.1; 435/252.3; 435/69.1; 530/350; 536/23.2

(58) Field of Classification Search ................ 435/136, 435/320.1, 189, 252.3, 252.33, 252.34; 536/23.2; 530/350

See application file for complete search history.

(56) References Cited

FOREIGN PATENT DOCUMENTS

EP    0 366 922 A1    5/1990
EP    0 869 175 A2    10/1998

OTHER PUBLICATIONS

Ausubel, F., Current Protocols in Molecular Biology, Hybridization Analysis of DNA Blots, pp. 2.10.8-2.10.11.*
Raitio, M., et al., Database Swissprot Online Abstract No. XP-002206939 (1988), accession P08305.
Raitio, M., et al., Database Swissprot Online Abstract No. XP-002206940 (1995), accession P98002.
Raitio, M., et al., Database Swissprot Online Abstract No. XP-002206941 (1988), accession P08306.
Raitio, M., et al., Database Swissprot Online Abstract No. XP-002206942 (1987), accession P06030.
Shapleigh, J.P., et al., Database Swissprot Online Abstract No. XP-002206943 (1994), accession P33517.
Cao, J., et al., Database Swissprot Online Abstract No. XP-002206944 (1994), accession Q03736.
Ludwig, et al., "A Kinetic Study of the Oxidation by Molecular Oxygen of the Cytochrome Chain of Intact Yeast Cells, *Acetobacter suboxydans* Cells, and of Particulate Suspensions of Heart Muscle," Enzyme, vol. 29, pp. 73-85 (1983).
Cao, et al., "Cytochrome aa3 of *Rhodobacter sphaeroides* as a Model for Mitochondrial Cytochrome c Oxidase," The Journal of Biological Chemistry, vol. 267(34), pp. 24273-24278 (1992).
Ostermeier, et al., "Structure at 2.7 Å resolution of the *Paracoccus denitrificans* two-subunit cytochrome c oxidase complexed with an antibody Fv fragment," Proc. Natl. Acad. Sci., vol. 94, pp. 10547-10553 (1997).
Raitio, M., et al., Database Swissprot Online Abstract No. XP-002206939, (Aug. 1, 1988).
Raitio, M., et al., Database Swissprot Online Abstract No. XP-002206940, (Nov. 1, 1995).
Raitio, M., et al., Database Swissprot Online Abstract No. XP-002206941, (Aug. 1, 1988).
Raitio, M., et al., Database Swissprot Online Abstract No. XP-002206942, (Aug. 13, 1987).
Raitio, M., et al., Database Swissprot Online Abstract No. XP-002206943, (Feb. 1, 1994).
Raitio, M., et al., Database Swissprot Online Abstract No. XP-002206944, (Feb. 1, 1994).
Ludwig, et al., "A Kinetic Study of the Oxidation by Molecular Oxygen of the Cytochrome Chain of Intact Yeast Cells, *Acetobacter suboxydans* Cells, and of Particulate Suspensions of Heart Muscle" Enzyme, vol. 29, pp. 73-85 (1983).
Cao, et al., "Cytochrome $aa_3$ of *Rhodobacter sphaeroides* as a Model for Mitochondrial Cytochrome c Oxidase," The Journal of Biological Chemistry, vol. 267(34), pp. 24273-24278 (1992).
Ostermeier, et al., "Structure at 2.7 Å resolution of the *Paracoccus denitrificans* two-submit cytochrome c oxidase complexed with an antibody $F_v$ fragment," Proc. Natl. Acad. Sci., vol. 94, pp. 10547-10553 (1997).

* cited by examiner

*Primary Examiner*—Delia M Ramirez
(74) *Attorney, Agent, or Firm*—Hoxie & Associates LLC

(57) ABSTRACT

The present invention is directed to a novel cytochrome c oxidase complex, genetic materials useful for the preparation of the said complex, such as recombinant polypeptides involved in cytochrome c oxidase complex, recombinant DNA fragments, expression vectors, recombinant organisms and the like. Those novel cytochrome c oxidase complex and genetic materials may be originated from a microorganism having the identifying characteristics of *Gluconobacter oxydans* DSM 4025. The present invention also provides a method for the preparation of the said novel recombinant cytochrome c oxidase complex and a process for the production of 2-keto-L-gulonic acid (2KGA).

8 Claims, 9 Drawing Sheets

CO I

```
G.O./peptide                         KDIGLLYLVAAGVVGF
P.D.    1:MS-AQISDSIEEKRGFFTRWFMSTNHKDIGVLYLFTAGLAGLISVTLTVYMRMELQHPGVQYMC---LE-
R.S.    1:MADAAIHGHEHDRRGFFTRWFMSTNHKDIGVLYLFTGGLVGLISVAFTVYMRMELMAPGVQFMCAEHLES
B.M.    1:-------------M-FINRWLFSTNHKDIGTLYLLFGAWAGMVG---TA-LSL-L----IR---AE-L--

P.D.   71:GM-R-LVAD--AAA-E-CTPNAHLWNVVVTY-HGILMMFFVVIPALFGGFGNYFMPLHIGAPDMAFPRLN
R.S.   71:GLVKGFFQSLWPSAVENCTPNGHLWNVMI-YGHGILMMFFVVIPALFGGFGNYFMPLHIGAPDMAFPRMN
B.M.   71:GQ-PG---TL----LGD---D-QIYNVVVT-AHAFVMIFFMVMPIMIGGFGNWLVPLMIGAPDMAFPRMN

P.D.  141:NLSYWLYVCGVSLAIASLLSPGGSDQPGAGVGWVLYPPL-ST-TEAGYAMDLAIFAVHVSGATSILGAIN
R.S.  141:NLSYWLYVAGTSLAVASLFAPGGNGQLGSGIGWVLYPPL-ST-SESGYSTDLAIFAVHLSGASSILGAIN
B.M.  141:NMSFWLLPPSFLLLLASSMVEAG---AGT--GWTVYPPLAGNLAHAGASVDLTIFSLHLAGVSSILGAIN

P.D.  211:IITTFLNMRAPGMTLFKVPLFAWAVFITAWMILLSLPVLAGGITMLLMDRNFGTQFFDPAGGDPVLYQH
R.S.  211:MITTFLMNRAPGMTMHKVPLFAWSIFVTAWLILLALPVLAGAITMLLTDRNFGTTFFQPSGGGDPVLYQH
B.M.  211:FITTIINMKPPAMSQYQTPLFVWSVMITAVLLLLSLPVLAAGITMLLTDRNLNTTFFDPAGGGDPILYQH

G.O./PCR      WFFGHPEVYIIILPGFGIISHVVSTFS-KKPVFGYLPMVYAMLAIGVLGFVVWAHHM
              >>>>>>                                       <<<<<<
P.D.  281:ILWFFGHPEVYMLILPGFGIISHVISTF-ARKPIFGYLPMVLAMAAIAFLGFIVWAHHMYTAGMSLTQQT
R.S.  281:ILWFFGHPEVYIIVLPAFGIVSHVIATF-AKKPIFGYLPMVYAMVAIGVLGFVVWAHHMYTAGLSLTQQS
B.M.  281:LFWFFGHPEVYILILPGFGMISHIVTYYSGKKEPFGYMGMVWAMMSIGFLGFIVWAHHMFTVGMDVDTRA

P.D.  351:YFQMATMTIAVPTGIKVFSWIATMWGGSIEFKTPMLWALA--FLFTVGGVTGVVIAQGSLDRVYHDTYYI
R.S.  351:YFMMATMVIAVPTGIKIFSWIATMWGGSIELKTPMLWALGFLFLFTVGGVTGIVLSQASVDRYYHDTYYV
B.M.  351:YFTSATMIIAIPTGVKVFSWLATLHGGNIKWSPAMMWALGFIFLFTVGGLTGIVLANSSLDIVLHDTYYV

P.D.  421:VAHFHYVMSLGALFAIFAGTYYSIGKMSGRQYPE-WAGQLHFWMMFIGSNLIFFPQHFLGRQGMPRRYID
R.S.  421:VAHFHYVMSLGAVFGIFAGSTSGIGKMSGRQYPE-WAGKLHFWMMFVGANLTFFPQHFLGRQGMPRRYID
B.M.  421:VAHFHYVLSMGAVPAIMGGFVHWFPLFSGYTLNDTWA-KIHFAIMFVGVNMTFFPQHFLGLSGMPRRYSD

P.D.  491:YPVEFSYWNNISSIGAYISFASFLFFIGIVFYTLFAGKPVNVPNYWNEHADTLEWTLPSPPPEHTFETLP
R.S.  491:YPEAFATWNFVSSLGAFLSFASFLFFLGVIFYSL-SGARVTANNYWNEHADTLEWTLTSPPPEHTFEQLP
B.M.  491:YPDAYTMWNTISSMGSFISLTAVMLMV-FIIWEAFASKR-EVLTV-DLTTTNLEWLNGCPPPYHTFEE-P

P.D.  561:KPEDWDRAQAHR
R.S.  561:KREDWERAPAH-
B.M.  561:TYVN-LK-----
```

Abbreviations: G.O. *G. oxydans* DSM4025; P.D. *Paracoccus denitrificans*;
R.S. *Rhodobacter sphaeroides*; B.M. Bovine (Mitochondria).
>>>>>>  <<<<<< : amino acid sequences for PCR primers (Fig. 6)
G.O./peptide: amino acid sequence from the purified enzyme
G.O./PCR: amino acid sequence deduced from DNA amplified by PCR (PCR/DNA)

Figure 3

COII

```
P.D.            1:MAIATKRRGVAAVMSLGVATMTAVPALAQDVLGDLPVIGKPVNGGMNFQPASSPLAHDQQWLDHFVLYII
R.S.            1:MRHSTTLTPCATGAA-GLLAATAAAA-QQQTL-E--IIGRPQPGGTGFHGSASPVATQIHWLDGFILVII
B.M.            1:---------------------MAYPM-Q--LG-FQDATSPIM--EELLHFHD-HT---L-MIVF-L--I

G.O./peptide                          KASQFTHNTPLEIVWTIVPV
G.O./PCR                              QFTHNTPLEIVWTIVPVVILVFIGAFSLPVLFKQQEFPE-GDI
                                      >>>>>>
P.D.           71:TAVTIFVCLLLLICIVRFNRRANPVPARFTHNTPIEVIWTLVPVLILVAIGAFSLPILFRSQEMPNDPDL
R.S.           71:GAITIFVTLLILYAVWRFHEKRNKVPARFTHNSPLEIAWTIVPIVILVAIGAFSLPVLFNQQEIP-EADE
B.M.           71:SSLVLYIISLIL--TTKLTHTSTMDP----QE--VETIWTILPAIILILIALPSLRILYMMDEI-NNPSL G.O./PCR           VINVEGRSWYWGYE
                      <<<<<<
P.D.          141:VIKAIGHQWYWSYEYPNDAFAFDALML-------E-K------E-ALADAGYSEDEYLLATDNPVVVPVG
R.S.          141:TVKVTGYQWYWGYEYPDEEISFESYMIGSPATGGDNRM-SPEVEQQLIEAGYTRDEFLLATDTAMVVPVN
B.M.          141:TVKTMGHQWYWSYEY----TDY-EDL--S--L-D-SYM-IPTSE--L-KPG---ELRLLEVDNRVVLPME P.D.          211:KKVLVQVTATDVIHAWTIPAFAVKQDAVPGRIAQLWFSVDQEGVYFGQCSELCGINHAYMPIVVKAVSQE
R.S.          211:KTVVVQVTGADVIHSWTVP-FGVRQDAVPGRLAQLWFRAEREGIFFGQCSELCGISHAYMPITVKVVSEE
B.M.          211:MTIRMLVSSGDVLHSWAVPSLGLKTDAIPGRLNQTTLMSSRPGLYYGQCSEICGSNHSFMPIVLELVPLK P.D.          281:KYEAWLAGAKEEFAADASDYLPASPVKLASAE
R.S.          281:AYAAWLEQARGG-TYELSSVLPATPAGV-SVE
B.M.          281:YFEKW-SASML---------------------
```

Abbreviations: G.O. G. oxydans DSM4025; P.D. Paracoccus denitrificans;
R.S. Rhodobacter sphaeroides; B.M. Bovine (Mitochondria).
>>>>>>  <<<<<< : amino acid sequences for PCR primers (Fig. 6)
G.O./peptide: amino acid sequence from the purified enzyme
G.O./PCR: amino acid sequence deduced from DNA amplified by PCR (PCR/DNA)

Figure 4

CO III

```
P.D.       1:MAHVKNHDYQILPPSIWPFFGAIGAFVMLTGAVAWMKGITFFGLPVEGPWMFLIGLVGVLYVMFGWWADV
R.S.       1:MAHAKNHDYHILPPSIWPFMASVGAFVMLNGAVLWMH-----G-S--GPWMGLIGLVVVLYTMFGWWSDV
B.M.       1:MTH-QTHAYHMVNPSPWPLTGALSALLMTSGLTMW---FHFNSMTL----L-MIGLTTNMLTMYQWWRDV

P.D.      71:VNE-GETGEHTPVVRIGLQYGFILFIMSEVMFFVAWFWAFIKNALYPMGPDSPIKDGVMPPEGIVTFDPW
R.S.      71:VTE-SLEGDHTPVVRLGLRWGFILFIMSEVIFFSAWFWSFFKHALYPMGPESPIIDGIFPPEGIITFDPW
B.M.      71:IRESTFQGHHTPAVQKGLRYGMILFIISEVLFFTGFFWAFYHSSL---AP-TPELGGCWPPTGIHPLNPL

G.O./PCR                TWAHHA-IVHGDRKKTAIGLAIAIGLGWIFTLCQAYEYYEIVHTEXXXXXXX
                        >>>>>>
P.D.     141:HLPLINTLILLLSGVAVTWAHHAFVLEGDRKTTINGLIVAVILGVCFTGLQAYEYSHAAFGLADTVYAG
R.S.     141:HLPLINTLILLCSGCAATWAHHALVHENNRRDVAWGLALAIALGALFTVFQAYEYSHAAFGFAGTIYGA
B.M.     141:EVPLLNTSVLLASGVSITWAHHS-LMEGDRKHMLQALFITITLGVYFTLLQASEYYEAPFTISDGVYGS

G.O./PCR           XXXXXXXXXXXXXXXXXD-SIFLLVCLIRILRGAMSAKQHVGFEMAAWYWHFV
                                              <<<<<<<
P.D.     211:AFYMATGFHGAHVIIGTIFLFVCLIRLLKGAMTQKQHVGFEAAAWYWHFVDVVWLFLFVVIYIWGR
R.S.     211:NFFMATGFHGFHVIVGTIFLLVCLIRVQRGHFTPEKHVGFEAAMWYWHFVDVVWLFLFASIYIWGQ
B.M.     211:TFFVATGFHGLHVIIGSTFLIVCFFRQLKFHFTSNHHFGFEAGAWYWHFVDVVWLFLYVSIYWWGS
```

Abbreviations: G.O. *G. oxydans* DSM4025; P.D. *Paracoccus denitrificans*;
R.S. *Rhodobacter sphaeroides*; B.M. Bovine (Mitochondria).
>>>>>>  <<<<<< : amino acid sequences for PCR primers (Fig. 6)
G.O./PCR:   amino acid sequence deduced from DNA amplified by PCR (PCR/DNA)

Figure 5

CO I     (target size: approx. 180 bp DNA)

A:
```
        W   F   F   G   H   P  ──►         *
     5'-TGGTTCTTCGGNCACCC-3'
          T   T       T
```

B:
```
     ◄── V   W   A   H   H   M              *
     3'-CANACCCGNGTAGTATAC-5'
            G              G
```

CO II     (target size: approx. 180 bp DNA)

A:
```
          Q   F   T   H   N   T  ──►      **
     5'-CAATTTACNCATAATAC-3'
          G   C       C   C
```

B:
```
     ◄── W   Y   W   G   Y   E   Y          *
     3'-ACCATAACCCCNATACTTAT-5'
                  G       G   C
```

CO III     (target size: approx. 300 bp DNA)

A:
```
          T   W   A   H   H   A  ──►       *
     5'-CANTGGGCNCATCATGC-3'
                  C       C
```

B:
```
     ◄── W   Y   W   H   F   V   D         *
     3'-ACCATAACCGTAAAACANCT-5'
                  G       G   G
```

```
     N   : A, T, G, C
     *   : based on consensus sequence
     **  : based on the peptide sequence
```

Figure 6

8.0 kb *Pst*I fragment containing CO I ORF of pUCO01
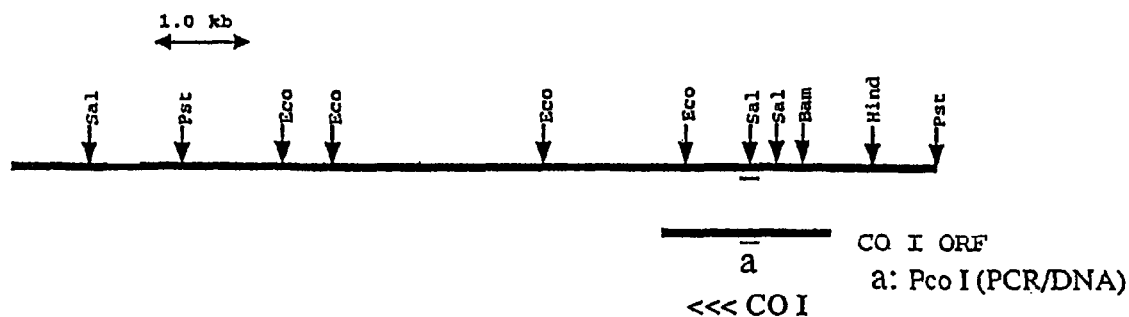
9.3 kb *Eco*RI fragment containing CO II and III ORFs of pUCO23
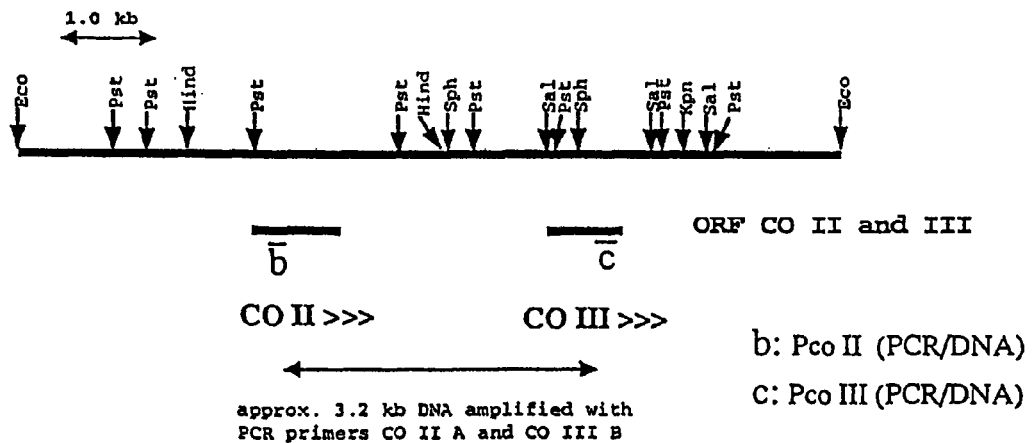
Figure 7

```
B.M. : --------------M-FINRWLFSTNHKDIGTLYLLFGAWAGMVGTALSLLIRAELGQPG--TL----L------G--D-
P.D. : MS-AQI-SDSIEEKRGFFTRWFMSTNHKDIGVLYLFTAGLAGLISVTLTVYMRMELQHPGVQYMC---LE-GM-R-LV-A
R.S. : MADAAIHGHE-HDRRGFFTRWFMSTNHKDIGVLYLFTGGLVGLISVAFTVYMRMELMAPGVQFMCAEHLESGLVKGFFQS
G.O. : MADAAIHGHDHHEKQGFFTRWFMSTNHKDIGLLYLVAAGVVGFISVLFTVYMRLELMDPGVQYMC---LE-G-AR--L--

B.M. : -----------D-QIYNVVVT-AHAFVMIFFMVMPIMIGGFGNWLVPLMIGAPDMAFPRMNNMSFWLLPPSFLLLLASSM
P.D. : ---DAAAECTPNAHLWNVVVTY-HGILMMFFVVIPALFGGFGNYFMPLHIGAPDMAFPRLNNLSYWLYVCGVSLAIASLL
R.S. : LWPSAVENCTPNGHLWNVMI-YGHGILMMFFVVIPALFGGFGNYFMPLHIGAPDMAFPRMNNLSYWLYVAGTSLAVASLF
G.O. : I-ADASQTCTANGHLWNVMVTY-HGILMMFFVGIPALFGGFGNYLMPLQIGAPDMAFPRMNNLSFWLFIAGTAMGVASLF

B.M. : VEAG---AGT--GWTVYPPLAGNLAHAGASVDLTIFSLHLAGVSSILGAINFITTIINMKPPAMSQYQTPLFVWSVMITA
P.D. : SPGGSDQPGAGVGWVLYPPL-ST-TEAGYAMDLAIPAVHVSGATSILGAINIITTFLNMRAPGMTLFKVPLFAWAVFITA
R.S. : APGGNGQLGSGIGWVLYPPL-ST-SESGYSTDLAIFAVHLSGASSILGAINMITTFLNMRAPGMTMHKVPLFANSIPVTA
G.O. : APGGDGQLGSGVGWVLYPPL-ST-REAGYSMDLAIFAVHLSGASSIMGAINMITTFLNMRAPGMTLHKVPLFSWSIFITA

B.M. : VLLLLSLPVLAAGITMLLTDRNLNTTFFDPAGGGDPILYQHLFWFFGHPEVYILILPGFGMISHIVTYYSGKKEPFGYMG
P.D. : WMILLSLPVLAGGITMLLMDRNFGTQFFDPAGGGDPVLYQHILWFFGHPEVYMLILPGFGIISHVISTF-ARKPIFGYLP
R.S. : WLILLALPVLAGAITMLLTDRNFGTTFFQPSGGGDPVLYQHILWFFGHPEVYIIVLPAFGIVSHVIATF-AKKPIFGYLP
G.O. : WLILLALPVLAGAITMLLTDRNFGTTFFNPAGGGDPILYQHILWFFGHPEVYIIILPGFGIISHVVSTF-SKKPVFGYLP

B.M. : MVWAMMSIGFLGFIVWAHHMFTVGMDVDTRAYFTSATMIIAIPTGVKVFSWLATLHGGNIKWSPAMMIALGFIFLFTVGG
P.D. : MVLAMAAIAFLGFIVWAHHMYTAGMSLTQQTYFQMATMIIAIPTGVKVFSWIATMWGGSIEFKTPMLWA--LAFLFTVGG
R.S. : MVYAMVAIGVLGFVVWAHHMYTAGLSLTQQSYFMMATMNIAVPTGIKIFSWIATMWGGSIELKTPMLWALGFLFLFTVGG
G.O. : MVYAMVAIGVLGFVVWAHHMYTVGMSLTQQSYFMLATMVIAVPTGIKIFSWIATMWGGSVEFKSPMLWAFGFMFLFTVGG

B.M. : LTGIVLANSSLDIVLHDTYYVVAHFHYVLSMGAVFAIMGGFVHWFPLFSGYTLNDTWA-KIHFAIMFVGVNMTFFPQHFL
P.D. : VTGVVIAQGSLDRVYHDTYYIVAHFHYVMSLGALFAIFAGTYYSIGKMSG-RQYPEWAGQLHFWMMFIGSNLIFFPQHFL
R.S. : VTGVVLSQASVDRYYHDTYYVVAHFHYVMSLGAVFGIFAGSTSGIGKMSG-RQYPEWAGKLHFWMMFVGANLTFFPQHFL
G.O. : VTGIVLAQAGLDRAYHDTYYVVAHFHYVMSLGAIFAIFAGIYFYMPKFSG-RAFPEWAAKLHFWTFFIGANVTFFPQHFL

B.M. : GLSGMPRRYSDYPDAYTMWNTISSMGSPISLTAVM-L--MVFIIWEAFASKREVLTV-DLTTTNLEWLNGCPPPYHTFEE
P.D. : GRQGMPRRYIDYPVEFSYWNNISSIGAYISFASFLFFIGIVF-YTLFAGKPVNVPNYWNEHADTLEWTLPSPPPEHTFET
R.S. : GRQGMPRRYIDYPEAFATWNFVSSLGAFLSFASFLFFLGVIF-YSL-SGARVTANNYWNEHADTLEWTLTSPPPEHTFEQ
G.O. : GRQGMPRRYIDYPEAFALWNKVSSYGAFLAFASFLPFI-VIFVYTLVAGRRETRPNPWGEFADTLEWTLPSPPPAHTFET

B.M. : -PTYVN-LK-----
P.D. : LPKPEDWDRAQAHR
R.S. : LPKREDWERAPAH-
G.O. : LPKRSDWDKHPSH-
```

Homology among amino acid sequences of the CO I subunits of aa3-type cytochrome c oxidase

|       | B.M. | P.D. | R.S. |
|-------|------|------|------|
| P.D.  | 52.2 | -    | -    |
| R.S.  | 50.6 | 76.7 | -    |
| G.O.  | 53.3 | 76.0 | 78.7 |

[% homology]

Abbreviations: G.O. *G. oxydans* DSM4025; P.D. *Paracoccus denitrificans*; R.S. *Rhodobacter sphaeroides*; B.M. Bovine (Mitochondria)

Figure 8

SEQUENCE LISTING

<160> NUMBER OF SEQ ID NOS: 36

<210> SEQ ID NO 1
<211> LENGTH: 1674
<212> TYPE: DNA
<213> ORGANISM: Gluconobacter oxydans
<220> FEATURE:
<221> NAME/KEY: CDS
<222> LOCATION: (1)..(1674)
<223> OTHER INFORMATION:

<400> SEQUENCE: 1

```
atg gca gac gcc gcc att cac ggc cat gac cac cat gag aag caa ggc      48
Met Ala Asp Ala Ala Ile His Gly His Asp His His Glu Lys Gln Gly
1               5                   10                  15 ttc ttc acg cgc tgg ttc atg tcg acc aac cac aaa gac atc ggt ctg      96
Phe Phe Thr Arg Trp Phe Met Ser Thr Asn His Lys Asp Ile Gly Leu
            20                  25                  30 cta tac ctt gta gcg gct ggt gtt gtt ggt ttc att tcc gtc ctg ttc     144
Leu Tyr Leu Val Ala Ala Gly Val Val Gly Phe Ile Ser Val Leu Phe
        35                  40                  45 acc gtc tac atg cgc ctt gag ctg atg gat ccg ggt gtt cag tac atg     192
Thr Val Tyr Met Arg Leu Glu Leu Met Asp Pro Gly Val Gln Tyr Met
    50                  55                  60 tgc ctt gaa ggc gca cgt ctg atc gcg gat gcc tcg cag aca tgt acg     240
Cys Leu Glu Gly Ala Arg Leu Ile Ala Asp Ala Ser Gln Thr Cys Thr
65                  70                  75                  80 gcg aac gga cac ctg tgg aac gtc atg gtt acc tac cat ggt att ctg     288
Ala Asn Gly His Leu Trp Asn Val Met Val Thr Tyr His Gly Ile Leu
                85                  90                  95 atg atg ttc ttt gtg ggt atc ccc gca ttg ttc ggt ggt ttt ggt aac     336
Met Met Phe Phe Val Gly Ile Pro Ala Leu Phe Gly Gly Phe Gly Asn
```

-continued

```
                      100                 105                 110
tat ctg atg ccg ctg caa atc ggc gct ccg gat atg gcc ttc ccg cgt       384
Tyr Leu Met Pro Leu Gln Ile Gly Ala Pro Asp Met Ala Phe Pro Arg
            115                 120                 125 atg aac aac ctg tcg ttc tgg ctg ttc att gcc ggt acc gcg atg ggc       432
Met Asn Asn Leu Ser Phe Trp Leu Phe Ile Ala Gly Thr Ala Met Gly
        130                 135                 140 gtg gct tcg ctg ttc gca ccg ggc ggt gac ggt cag ctg ggt tcg ggc       480
Val Ala Ser Leu Phe Ala Pro Gly Gly Asp Gly Gln Leu Gly Ser Gly
145                 150                 155                 160 gtt ggt tgg gtt ctg tac ccg ccg ctg tcg acc cgc gaa gct ggc tat       528
Val Gly Trp Val Leu Tyr Pro Pro Leu Ser Thr Arg Glu Ala Gly Tyr
                165                 170                 175 tcg atg gac ctc gcg att ttc gcg gtt cac ttg tcg ggt gcc tcc tcg       576
Ser Met Asp Leu Ala Ile Phe Ala Val His Leu Ser Gly Ala Ser Ser
            180                 185                 190 atc atg ggc gcg atc aac atg atc acg acc ttc ttg aac atg cgc gcc       624
Ile Met Gly Ala Ile Asn Met Ile Thr Thr Phe Leu Asn Met Arg Ala
        195                 200                 205 ccc ggc atg acg ctg cac aaa gtg ccg ttg ttc tcg tgg tcg atc ttt       672
Pro Gly Met Thr Leu His Lys Val Pro Leu Phe Ser Trp Ser Ile Phe
    210                 215                 220 atc acg gct tgg ctg atc ctg ctg gcg ctg ccg gtt ctg gct ggt gca       720
Ile Thr Ala Trp Leu Ile Leu Leu Ala Leu Pro Val Leu Ala Gly Ala
225                 230                 235                 240 atc acc atg ctg ctg acc gac cgt aac ttc ggc acg acc ttc ttc aat       768
Ile Thr Met Leu Leu Thr Asp Arg Asn Phe Gly Thr Thr Phe Phe Asn
                245                 250                 255 cct gct ggc ggc ggt gac ccg att ctg tac caa cac atc ctg tgg ttc       816
Pro Ala Gly Gly Gly Asp Pro Ile Leu Tyr Gln His Ile Leu Trp Phe
            260                 265                 270 ttt ggg cac ccg gaa gtg tac atc atc att ctg ccc ggc ttt ggc atc       864
Phe Gly His Pro Glu Val Tyr Ile Ile Ile Leu Pro Gly Phe Gly Ile
        275                 280                 285 atc agc cat gtc gtg tcg acc ttc tcg aaa aag ccg gtc ttc ggt tac       912
Ile Ser His Val Val Ser Thr Phe Ser Lys Lys Pro Val Phe Gly Tyr
    290                 295                 300 ctg ccg atg gtc tat gca atg gtg gca atc ggt gtt ctg ggc ttt gtc       960
Leu Pro Met Val Tyr Ala Met Val Ala Ile Gly Val Leu Gly Phe Val
305                 310                 315                 320 gtc tgg gcg cac cac atg tac acc gtt ggt atg tcg ctg acc cag caa      1008
Val Trp Ala His His Met Tyr Thr Val Gly Met Ser Leu Thr Gln Gln
                325                 330                 335 tcc tac ttc atg ctg gcc acc atg gtg atc gcg gtg ccg acc ggc att      1056
Ser Tyr Phe Met Leu Ala Thr Met Val Ile Ala Val Pro Thr Gly Ile
            340                 345                 350 aag atc ttc tcg tgg atc gcc acg atg tgg ggc ggc tcg gtt gag ttc      1104
Lys Ile Phe Ser Trp Ile Ala Thr Met Trp Gly Gly Ser Val Glu Phe
        355                 360                 365 aaa tcg ccg atg ctc tgg gcc ttt ggc ttt atg ttc ctg ttc acc gtg      1152
Lys Ser Pro Met Leu Trp Ala Phe Gly Phe Met Phe Leu Phe Thr Val
    370                 375                 380 ggt ggt gtg acc ggt atc gtg ctg gcc caa gcg ggt ctg gac cgt gca      1200
Gly Gly Val Thr Gly Ile Val Leu Ala Gln Ala Gly Leu Asp Arg Ala
385                 390                 395                 400 tat cac gac acc tat tac gtg gtg gcg cac ttc cat tat gtg atg tcg      1248
Tyr His Asp Thr Tyr Tyr Val Val Ala His Phe His Tyr Val Met Ser
                405                 410                 415 ctg ggt gcg atc ttt gcg atc ttc gcc ggt atc tac ttt tac atg ccg      1296
```

```
Leu Gly Ala Ile Phe Ala Ile Phe Ala Gly Ile Tyr Phe Tyr Met Pro
            420                 425                 430 aag ttc tcg ggc cgc gct ttc ccg gaa tgg gct gca aag ctg cac ttc    1344
Lys Phe Ser Gly Arg Ala Phe Pro Glu Trp Ala Ala Lys Leu His Phe
        435                 440                 445 tgg acc ttc ttc atc ggt gcg aac gtc acg ttc ttc ccg cag cac ttc    1392
Trp Thr Phe Phe Ile Gly Ala Asn Val Thr Phe Phe Pro Gln His Phe
    450                 455                 460 ctg gga cgt cag ggt atg ccg cgc cgt tac atc gac tat ccc gaa gcc    1440
Leu Gly Arg Gln Gly Met Pro Arg Arg Tyr Ile Asp Tyr Pro Glu Ala
465                 470                 475                 480 ttc gcg ctg tgg aac aaa gtc tcg tcc tat ggt gcg ttc ctg gcc ttc    1488
Phe Ala Leu Trp Asn Lys Val Ser Ser Tyr Gly Ala Phe Leu Ala Phe
                485                 490                 495 gcc tcg ttc ctg ttc ttc atc gtg atc ttt gtc tat acg ctg gtt gct    1536
Ala Ser Phe Leu Phe Phe Ile Val Ile Phe Val Tyr Thr Leu Val Ala
                500                 505                 510 ggc cgc cgc gag acc cgt ccg aac ccg tgg ggc gaa ttc gcc gat acg    1584
Gly Arg Arg Glu Thr Arg Pro Asn Pro Trp Gly Glu Phe Ala Asp Thr
            515                 520                 525 ctg gaa tgg acg ctg cca tca ccg cct ccg gcc cac acg ttc gaa acg    1632
Leu Glu Trp Thr Leu Pro Ser Pro Pro Pro Ala His Thr Phe Glu Thr
530                 535                 540 ctg ccc aag cgc tcg gac tgg gac aag cat ccc tcg cac taa            1674
Leu Pro Lys Arg Ser Asp Trp Asp Lys His Pro Ser His
545                 550                 555

<210> SEQ ID NO 2
<211> LENGTH: 557
<212> TYPE: PRT
<213> ORGANISM: Gluconobacter oxydans

<400> SEQUENCE: 2

Met Ala Asp Ala Ala Ile His Gly His Asp His His Glu Lys Gln Gly
1               5                   10                  15

Phe Phe Thr Arg Trp Phe Met Ser Thr Asn His Lys Asp Ile Gly Leu
            20                  25                  30

Leu Tyr Leu Val Ala Ala Gly Val Gly Phe Ile Ser Val Leu Phe
        35                  40                  45

Thr Val Tyr Met Arg Leu Glu Leu Met Asp Pro Gly Val Gln Tyr Met
    50                  55                  60

Cys Leu Glu Gly Ala Arg Leu Ile Ala Asp Ala Ser Gln Thr Cys Thr
65                  70                  75                  80

Ala Asn Gly His Leu Trp Asn Val Met Val Thr Tyr His Gly Ile Leu
                85                  90                  95

Met Met Phe Phe Val Gly Ile Pro Ala Leu Phe Gly Phe Gly Asn
                100                 105                 110

Tyr Leu Met Pro Leu Gln Ile Gly Ala Pro Asp Met Ala Phe Pro Arg
            115                 120                 125

Met Asn Asn Leu Ser Phe Trp Leu Phe Ile Ala Gly Thr Ala Met Gly
        130                 135                 140

Val Ala Ser Leu Phe Ala Pro Gly Gly Asp Gly Gln Leu Gly Ser Gly
145                 150                 155                 160

Val Gly Trp Val Leu Tyr Pro Pro Leu Ser Thr Arg Glu Ala Gly Tyr
                165                 170                 175

Ser Met Asp Leu Ala Ile Phe Ala Val His Leu Ser Gly Ala Ser Ser
            180                 185                 190
```

```
Ile Met Gly Ala Ile Asn Met Ile Thr Thr Phe Leu Asn Met Arg Ala
            195                 200                 205

Pro Gly Met Thr Leu His Lys Val Pro Leu Phe Ser Trp Ser Ile Phe
210                 215                 220

Ile Thr Ala Trp Leu Ile Leu Ala Leu Pro Val Leu Ala Gly Ala
225                 230                 235                 240

Ile Thr Met Leu Leu Thr Asp Arg Asn Phe Gly Thr Thr Phe Phe Asn
            245                 250                 255

Pro Ala Gly Gly Asp Pro Ile Leu Tyr Gln His Ile Leu Trp Phe
                260                 265                 270

Phe Gly His Pro Glu Val Tyr Ile Ile Leu Pro Gly Phe Gly Ile
                275                 280                 285

Ile Ser His Val Val Ser Thr Phe Ser Lys Lys Pro Val Phe Gly Tyr
            290                 295                 300

Leu Pro Met Val Tyr Ala Met Val Ala Ile Gly Val Leu Gly Phe Val
305                 310                 315                 320

Val Trp Ala His His Met Tyr Thr Val Gly Met Ser Leu Thr Gln Gln
                325                 330                 335

Ser Tyr Phe Met Leu Ala Thr Met Val Ile Ala Val Pro Thr Gly Ile
                340                 345                 350

Lys Ile Phe Ser Trp Ile Ala Thr Met Trp Gly Gly Ser Val Glu Phe
            355                 360                 365

Lys Ser Pro Met Leu Trp Ala Phe Gly Phe Met Phe Leu Phe Thr Val
            370                 375                 380

Gly Gly Val Thr Gly Ile Val Leu Ala Gln Ala Gly Leu Asp Arg Ala
385                 390                 395                 400

Tyr His Asp Thr Tyr Tyr Val Val Ala His Phe His Tyr Val Met Ser
                405                 410                 415

Leu Gly Ala Ile Phe Ala Ile Phe Ala Gly Ile Tyr Phe Tyr Met Pro
                420                 425                 430

Lys Phe Ser Gly Arg Ala Phe Pro Glu Trp Ala Ala Lys Leu His Phe
            435                 440                 445

Trp Thr Phe Phe Ile Gly Ala Asn Val Thr Phe Phe Pro Gln His Phe
            450                 455                 460

Leu Gly Arg Gln Gly Met Pro Arg Arg Tyr Ile Asp Tyr Pro Glu Ala
465                 470                 475                 480

Phe Ala Leu Trp Asn Lys Val Ser Ser Tyr Gly Ala Phe Leu Ala Phe
                485                 490                 495

Ala Ser Phe Leu Phe Phe Ile Val Ile Phe Val Tyr Thr Leu Val Ala
                500                 505                 510

Gly Arg Arg Glu Thr Arg Pro Asn Pro Trp Gly Glu Phe Ala Asp Thr
            515                 520                 525

Leu Glu Trp Thr Leu Pro Ser Pro Pro Ala His Thr Phe Glu Thr
530                 535                 540

Leu Pro Lys Arg Ser Asp Trp Asp Lys His Pro Ser His
545                 550                 555
```

<210> SEQ ID NO 3
<211> LENGTH: 132
<212> TYPE: DNA
<213> ORGANISM: Gluconobacter oxydans
<220> FEATURE:
<221> NAME/KEY: CDS
<222> LOCATION: (1)..(132)
<223> OTHER INFORMATION:

```
<400> SEQUENCE: 3 ccg ctg gaa atc gtc tgg acg att gtt ccg gtt gtg att ctg gtc ttc      48
Pro Leu Glu Ile Val Trp Thr Ile Val Pro Val Val Ile Leu Val Phe
1               5                   10                  15 atc ggt gcg ttc tcg ctg ccg gtg ctg ttc aaa cag caa gag ttc ccc      96
Ile Gly Ala Phe Ser Leu Pro Val Leu Phe Lys Gln Gln Glu Phe Pro
            20                  25                  30 gag ggt gac atc gtc atc aac gtc gag ggt cgt agc                      132
Glu Gly Asp Ile Val Ile Asn Val Glu Gly Arg Ser
        35                  40

<210> SEQ ID NO 4
<211> LENGTH: 44
<212> TYPE: PRT
<213> ORGANISM: Gluconobacter oxydans

<400> SEQUENCE: 4

Pro Leu Glu Ile Val Trp Thr Ile Val Pro Val Val Ile Leu Val Phe
1               5                   10                  15

Ile Gly Ala Phe Ser Leu Pro Val Leu Phe Lys Gln Gln Glu Phe Pro
            20                  25                  30

Glu Gly Asp Ile Val Ile Asn Val Glu Gly Arg Ser
        35                  40

<210> SEQ ID NO 5
<211> LENGTH: 114
<212> TYPE: DNA
<213> ORGANISM: Gluconobacter oxydans
<220> FEATURE:
<221> NAME/KEY: CDS
<222> LOCATION: (1)..(114)
<223> OTHER INFORMATION:

<400> SEQUENCE: 5 atc gtc cac ggc gac cgc aag aaa acc gcg att ggc cta gcg att gcc      48
Ile Val His Gly Asp Arg Lys Lys Thr Ala Ile Gly Leu Ala Ile Ala
1               5                   10                  15 atc ggc ctt ggc tgg atc ttt acc ctg tgc caa gcc tat gaa tat tat      96
Ile Gly Leu Gly Trp Ile Phe Thr Leu Cys Gln Ala Tyr Glu Tyr Tyr
            20                  25                  30 gaa atc gtc cat acc gaa                                              114
Glu Ile Val His Thr Glu
        35

<210> SEQ ID NO 6
<211> LENGTH: 38
<212> TYPE: PRT
<213> ORGANISM: Gluconobacter oxydans

<400> SEQUENCE: 6

Ile Val His Gly Asp Arg Lys Lys Thr Ala Ile Gly Leu Ala Ile Ala
1               5                   10                  15

Ile Gly Leu Gly Trp Ile Phe Thr Leu Cys Gln Ala Tyr Glu Tyr Tyr
            20                  25                  30

Glu Ile Val His Thr Glu
        35

<210> SEQ ID NO 7
<211> LENGTH: 87
<212> TYPE: DNA
<213> ORGANISM: Gluconobacter oxydans
<220> FEATURE:
<221> NAME/KEY: CDS
```

-continued

```
<222> LOCATION: (1)..(87)
<223> OTHER INFORMATION:

<400> SEQUENCE: 7 gat tcg atc ttc ctg ctg gtc tgc ctg atc cgc atc ctg cgc ggt gcg      48
Asp Ser Ile Phe Leu Leu Val Cys Leu Ile Arg Ile Leu Arg Gly Ala
1               5                   10                  15 atg tcg gca aaa cag cac gtc ggt ttc gag atg gcc gca                  87
Met Ser Ala Lys Gln His Val Gly Phe Glu Met Ala Ala
            20                  25

<210> SEQ ID NO 8
<211> LENGTH: 29
<212> TYPE: PRT
<213> ORGANISM: Gluconobacter oxydans

<400> SEQUENCE: 8

Asp Ser Ile Phe Leu Leu Val Cys Leu Ile Arg Ile Leu Arg Gly Ala
1               5                   10                  15

Met Ser Ala Lys Gln His Val Gly Phe Glu Met Ala Ala
            20                  25

<210> SEQ ID NO 9
<211> LENGTH: 6
<212> TYPE: PRT
<213> ORGANISM: Rhodobacter sphaeroides

<400> SEQUENCE: 9

Trp Phe Phe Gly His Pro
1               5

<210> SEQ ID NO 10
<211> LENGTH: 6
<212> TYPE: PRT
<213> ORGANISM: Rhodobacter sphaeroides

<400> SEQUENCE: 10

Val Trp Ala His His Met
1               5

<210> SEQ ID NO 11
<211> LENGTH: 16
<212> TYPE: PRT
<213> ORGANISM: Gluconobacter oxydans
<220> FEATURE:
<221> NAME/KEY: PEPTIDE
<222> LOCATION: (1)..(16)
<223> OTHER INFORMATION:

<400> SEQUENCE: 11

Lys Asp Ile Gly Leu Leu Tyr Leu Val Ala Ala Gly Val Val Gly Phe
1               5                   10                  15

<210> SEQ ID NO 12
<211> LENGTH: 168
<212> TYPE: DNA
<213> ORGANISM: Gluconobacter oxydans
<220> FEATURE:
<221> NAME/KEY: CDS
<222> LOCATION: (1)..(168)
<223> OTHER INFORMATION:

<400> SEQUENCE: 12 tgg ttt ttt gga cac ccg gaa gtg tac atc atc att ctg ccc ggc ttt      48
Trp Phe Phe Gly His Pro Glu Val Tyr Ile Ile Ile Leu Pro Gly Phe
1               5                   10                  15
```

```
ggc atc atc agc cat gtc gtg tcg acc ttc tcg aaa aag ccg gtc ttc      96
Gly Ile Ile Ser His Val Val Ser Thr Phe Ser Lys Lys Pro Val Phe
             20                  25                  30 ggt tac ctg ccg atg gtc tat gca atg ttg gca atc ggt gtt ctg ggc     144
Gly Tyr Leu Pro Met Val Tyr Ala Met Leu Ala Ile Gly Val Leu Gly
         35                  40                  45 ttt gtc gtg tgg gcg cac cat atg                                     168
Phe Val Val Trp Ala His His Met
 50                  55
```

<210> SEQ ID NO 13
<211> LENGTH: 56
<212> TYPE: PRT
<213> ORGANISM: Gluconobacter oxydans

<400> SEQUENCE: 13

```
Trp Phe Phe Gly His Pro Glu Val Tyr Ile Ile Ile Leu Pro Gly Phe
 1               5                  10                  15

Gly Ile Ile Ser His Val Val Ser Thr Phe Ser Lys Lys Pro Val Phe
             20                  25                  30

Gly Tyr Leu Pro Met Val Tyr Ala Met Leu Ala Ile Gly Val Leu Gly
         35                  40                  45

Phe Val Val Trp Ala His His Met
 50                  55
```

<210> SEQ ID NO 14
<211> LENGTH: 20
<212> TYPE: PRT
<213> ORGANISM: Gluconobacter oxydans
<220> FEATURE:
<221> NAME/KEY: PEPTIDE
<222> LOCATION: (1)..(20)
<223> OTHER INFORMATION:

<400> SEQUENCE: 14

```
Lys Ala Ser Gln Phe Thr His Asn Thr Pro Leu Glu Ile Val Trp Thr
 1               5                  10                  15

Ile Val Pro Val
             20
```

<210> SEQ ID NO 15
<211> LENGTH: 6
<212> TYPE: PRT
<213> ORGANISM: Gluconobacter oxydans

<400> SEQUENCE: 15

```
Gln Phe Thr His Asn Thr
 1               5
```

<210> SEQ ID NO 16
<211> LENGTH: 7
<212> TYPE: PRT
<213> ORGANISM: Rhodobacter sphaeroides

<400> SEQUENCE: 16

```
Trp Tyr Trp Gly Tyr Glu Tyr
 1               5
```

<210> SEQ ID NO 17
<211> LENGTH: 6
<212> TYPE: PRT
<213> ORGANISM: Rhodobacter sphaeroides

```
<400> SEQUENCE: 17

Thr Trp Ala His His Ala
1               5

<210> SEQ ID NO 18
<211> LENGTH: 7
<212> TYPE: PRT
<213> ORGANISM: Rhodobacter sphaeroides

<400> SEQUENCE: 18

Trp Tyr Trp His Phe Val Asp
1               5

<210> SEQ ID NO 19
<211> LENGTH: 554
<212> TYPE: PRT
<213> ORGANISM: Paracoccus denitrificans

<400> SEQUENCE: 19

Met Ser Ala Gln Ile Ser Asp Ser Ile Glu Glu Lys Arg Gly Phe Phe
1               5                   10                  15

Thr Arg Trp Phe Met Ser Thr Asn His Lys Asp Ile Gly Val Leu Tyr
            20                  25                  30

Leu Phe Thr Ala Gly Leu Ala Gly Leu Ile Ser Val Thr Leu Thr Val
        35                  40                  45

Tyr Met Arg Met Glu Leu Gln His Pro Gly Val Gln Tyr Met Cys Leu
    50                  55                  60

Glu Gly Met Arg Leu Val Ala Asp Ala Ala Glu Cys Thr Pro Asn
65                  70                  75                  80

Ala His Leu Trp Asn Val Val Thr Tyr His Gly Ile Leu Met Met
                85                  90                  95

Phe Phe Val Val Ile Pro Ala Leu Phe Gly Gly Phe Gly Asn Tyr Phe
                100                 105                 110

Met Pro Leu His Ile Gly Ala Pro Asp Met Ala Phe Pro Arg Leu Asn
            115                 120                 125

Asn Leu Ser Tyr Trp Leu Tyr Val Cys Gly Val Ser Leu Ala Ile Ala
        130                 135                 140

Ser Leu Leu Ser Pro Gly Gly Ser Asp Gln Pro Gly Ala Gly Val Gly
145                 150                 155                 160

Trp Val Leu Tyr Pro Pro Leu Ser Thr Thr Glu Ala Gly Tyr Ala Met
                165                 170                 175

Asp Leu Ala Ile Phe Ala Val His Val Ser Gly Ala Thr Ser Ile Leu
            180                 185                 190

Gly Ala Ile Asn Ile Ile Thr Thr Phe Leu Asn Met Arg Ala Pro Gly
        195                 200                 205

Met Thr Leu Phe Lys Val Pro Leu Phe Ala Trp Ala Val Phe Ile Thr
    210                 215                 220

Ala Trp Met Ile Leu Leu Ser Leu Pro Val Leu Ala Gly Gly Ile Thr
225                 230                 235                 240

Met Leu Leu Met Asp Arg Asn Phe Gly Thr Gln Phe Phe Asp Pro Ala
                245                 250                 255

Gly Gly Gly Asp Pro Val Leu Tyr Gln His Ile Leu Trp Phe Phe Gly
            260                 265                 270

His Pro Glu Val Tyr Met Leu Ile Leu Pro Gly Phe Gly Ile Ile Ser
        275                 280                 285

His Val Ile Ser Thr Phe Ala Arg Lys Pro Ile Phe Gly Tyr Leu Pro
```

```
                  290                 295                 300
Met Val Leu Ala Met Ala Ile Ala Phe Leu Gly Phe Ile Val Trp
305                 310                 315                 320

Ala His His Met Tyr Thr Ala Gly Met Ser Leu Thr Gln Gln Thr Tyr
                325                 330                 335

Phe Gln Met Ala Thr Met Thr Ile Ala Val Pro Thr Gly Ile Lys Val
                340                 345                 350

Phe Ser Trp Ile Ala Thr Met Trp Gly Gly Ser Ile Glu Phe Lys Thr
                355                 360                 365

Pro Met Leu Trp Ala Leu Ala Phe Leu Phe Thr Val Gly Gly Val Thr
370                 375                 380

Gly Val Val Ile Ala Gln Gly Ser Leu Asp Arg Val Tyr His Asp Thr
385                 390                 395                 400

Tyr Tyr Ile Val Ala His Phe His Tyr Val Met Ser Leu Gly Ala Leu
                405                 410                 415

Phe Ala Ile Phe Ala Gly Thr Tyr Tyr Ser Ile Gly Lys Met Ser Gly
                420                 425                 430

Arg Gln Tyr Pro Glu Trp Ala Gly Gln Leu His Phe Trp Met Met Phe
                435                 440                 445

Ile Gly Ser Asn Leu Ile Phe Phe Pro Gln His Phe Leu Gly Arg Gln
                450                 455                 460

Gly Met Pro Arg Arg Tyr Ile Asp Tyr Pro Val Glu Phe Ser Tyr Trp
465                 470                 475                 480

Asn Asn Ile Ser Ser Ile Gly Ala Tyr Ile Ser Phe Ala Ser Phe Leu
                485                 490                 495

Phe Phe Ile Gly Ile Val Phe Tyr Thr Leu Phe Ala Gly Lys Pro Val
                500                 505                 510

Asn Val Pro Asn Tyr Trp Asn Glu His Ala Asp Thr Leu Glu Trp Thr
                515                 520                 525

Leu Pro Ser Pro Pro Glu His Thr Phe Glu Thr Leu Pro Lys Pro
530                 535                 540

Glu Asp Trp Asp Arg Ala Gln Ala His Arg
545                 550

<210> SEQ ID NO 20
<211> LENGTH: 565
<212> TYPE: PRT
<213> ORGANISM: Rhodobacter sphaeroides

<400> SEQUENCE: 20

Met Ala Asp Ala Ala Ile His Gly His Glu His Asp Arg Arg Gly Phe
1               5                   10                  15

Phe Thr Arg Trp Phe Met Ser Thr Asn His Lys Asp Ile Gly Val Leu
                20                  25                  30

Tyr Leu Phe Thr Gly Gly Leu Val Gly Leu Ile Ser Val Ala Phe Thr
            35                  40                  45

Val Tyr Met Arg Met Glu Leu Met Ala Pro Gly Val Gln Phe Met Cys
50                  55                  60

Ala Glu His Leu Glu Ser Gly Leu Val Lys Gly Phe Phe Gln Ser Leu
65                  70                  75                  80

Trp Pro Ser Ala Val Glu Asn Cys Thr Pro Asn Gly His Leu Trp Asn
                85                  90                  95

Val Met Ile Tyr Gly His Gly Ile Leu Met Met Phe Phe Val Val Ile
                100                 105                 110
```

```
Pro Ala Leu Phe Gly Gly Phe Asn Tyr Phe Met Pro Leu His Ile
        115                 120                 125

Gly Ala Pro Asp Met Ala Phe Pro Arg Met Asn Asn Leu Ser Tyr Trp
        130                 135                 140

Leu Tyr Val Ala Gly Thr Ser Leu Ala Val Ala Ser Leu Phe Ala Pro
145                 150                 155                 160

Gly Gly Asn Gly Gln Leu Gly Ser Gly Ile Gly Trp Val Leu Tyr Pro
                165                 170                 175

Pro Leu Ser Thr Ser Glu Ser Gly Tyr Ser Thr Asp Leu Ala Ile Phe
                180                 185                 190

Ala Val His Leu Ser Gly Ala Ser Ser Ile Leu Gly Ala Ile Asn Met
            195                 200                 205

Ile Thr Thr Phe Leu Met Asn Arg Ala Pro Gly Met Thr Met His Lys
        210                 215                 220

Val Pro Leu Phe Ala Trp Ser Ile Phe Val Thr Ala Trp Leu Ile Leu
225                 230                 235                 240

Leu Ala Leu Pro Val Leu Ala Gly Ala Ile Thr Met Leu Leu Thr Asp
                245                 250                 255

Arg Asn Phe Gly Thr Thr Phe Phe Gln Pro Ser Gly Gly Gly Asp Pro
            260                 265                 270

Val Leu Tyr Gln His Ile Leu Trp Phe Phe Gly His Pro Glu Val Tyr
        275                 280                 285

Ile Ile Val Leu Pro Ala Phe Gly Ile Val Ser His Val Ile Ala Thr
        290                 295                 300

Phe Ala Lys Lys Pro Ile Phe Gly Tyr Leu Pro Met Val Tyr Ala Met
305                 310                 315                 320

Val Ala Ile Gly Val Leu Gly Phe Val Val Trp Ala His His Met Tyr
                325                 330                 335

Thr Ala Gly Leu Ser Leu Thr Gln Gln Ser Tyr Phe Met Met Ala Thr
            340                 345                 350

Met Val Ile Ala Val Pro Thr Gly Ile Lys Ile Phe Ser Trp Ile Ala
        355                 360                 365

Thr Met Trp Gly Gly Ser Ile Glu Leu Lys Thr Pro Met Leu Trp Ala
        370                 375                 380

Leu Gly Phe Leu Phe Leu Phe Thr Val Gly Gly Val Thr Gly Ile Val
385                 390                 395                 400

Leu Ser Gln Ala Ser Val Asp Arg Tyr Tyr His Asp Thr Tyr Tyr Val
                405                 410                 415

Val Ala His Phe His Tyr Val Met Ser Leu Gly Ala Val Phe Gly Ile
            420                 425                 430

Phe Ala Gly Ser Thr Ser Gly Ile Gly Lys Met Ser Gly Arg Gln Tyr
        435                 440                 445

Pro Glu Trp Ala Gly Lys Leu His Phe Trp Met Met Phe Val Gly Ala
        450                 455                 460

Asn Leu Thr Phe Phe Pro Gln His Phe Leu Gly Arg Gln Gly Met Pro
465                 470                 475                 480

Arg Arg Tyr Ile Asp Tyr Pro Glu Ala Phe Ala Thr Trp Asn Phe Val
                485                 490                 495

Ser Ser Leu Gly Ala Phe Leu Ser Phe Ala Ser Phe Leu Phe Phe Leu
            500                 505                 510

Gly Val Ile Phe Tyr Ser Leu Ser Gly Ala Arg Val Thr Ala Asn Asn
        515                 520                 525

Tyr Trp Asn Glu His Ala Asp Thr Leu Glu Trp Thr Leu Thr Ser Pro
```

```
                    530                 535                 540
Pro Pro Glu His Thr Phe Glu Gln Leu Pro Lys Arg Glu Asp Trp Glu
545                 550                 555                 560

Arg Ala Pro Ala His
                565

<210> SEQ ID NO 21
<211> LENGTH: 514
<212> TYPE: PRT
<213> ORGANISM: Bovine (Mitochondria)

<400> SEQUENCE: 21

Met Phe Ile Asn Arg Trp Leu Phe Ser Thr Asn His Lys Asp Ile Gly
1               5                   10                  15

Thr Leu Tyr Leu Leu Phe Gly Ala Trp Ala Gly Met Val Gly Thr Ala
                20                  25                  30

Leu Ser Leu Leu Ile Arg Ala Glu Leu Gly Gln Pro Gly Thr Leu Leu
            35                  40                  45

Gly Asp Asp Gln Ile Tyr Asn Val Val Val Thr Ala His Ala Phe Val
50                  55                  60

Met Ile Phe Phe Met Val Met Pro Ile Met Ile Gly Gly Phe Gly Asn
65                  70                  75                  80

Trp Leu Val Pro Leu Met Ile Gly Ala Pro Asp Met Ala Phe Pro Arg
                85                  90                  95

Met Asn Asn Met Ser Phe Trp Leu Leu Pro Pro Ser Phe Leu Leu Leu
            100                 105                 110

Leu Ala Ser Ser Met Val Glu Ala Gly Ala Gly Thr Gly Trp Thr Val
        115                 120                 125

Tyr Pro Pro Leu Ala Gly Asn Leu Ala His Ala Gly Ala Ser Val Asp
130                 135                 140

Leu Thr Ile Phe Ser Leu His Leu Ala Gly Val Ser Ser Ile Leu Gly
145                 150                 155                 160

Ala Ile Asn Phe Ile Thr Thr Ile Ile Asn Met Lys Pro Pro Ala Met
                165                 170                 175

Ser Gln Tyr Gln Thr Pro Leu Phe Val Trp Ser Val Met Ile Thr Ala
            180                 185                 190

Val Leu Leu Leu Leu Ser Leu Pro Val Leu Ala Ala Gly Ile Thr Met
        195                 200                 205

Leu Leu Thr Asp Arg Asn Leu Asn Thr Thr Phe Phe Asp Pro Ala Gly
210                 215                 220

Gly Gly Asp Pro Ile Leu Tyr Gln His Leu Phe Trp Phe Phe Gly His
225                 230                 235                 240

Pro Glu Val Tyr Ile Leu Ile Leu Pro Gly Phe Gly Met Ile Ser His
                245                 250                 255

Ile Val Thr Tyr Tyr Ser Gly Lys Lys Glu Pro Phe Gly Tyr Met Gly
            260                 265                 270

Met Val Trp Ala Met Met Ser Ile Gly Phe Leu Gly Phe Ile Val Trp
        275                 280                 285

Ala His His Met Phe Thr Val Gly Met Asp Val Asp Thr Arg Ala Tyr
290                 295                 300

Phe Thr Ser Ala Thr Met Ile Ile Ala Ile Pro Thr Gly Val Lys Val
305                 310                 315                 320

Phe Ser Trp Leu Ala Thr Leu His Gly Gly Asn Ile Lys Trp Ser Pro
                325                 330                 335
```

```
Ala Met Met Trp Ala Leu Gly Phe Ile Phe Leu Phe Thr Val Gly Gly
                340                 345                 350

Leu Thr Gly Ile Val Leu Ala Asn Ser Ser Leu Asp Ile Val Leu His
            355                 360                 365

Asp Thr Tyr Tyr Val Val Ala His Phe His Tyr Val Leu Ser Met Gly
        370                 375                 380

Ala Val Phe Ala Ile Met Gly Gly Phe Val His Trp Phe Pro Leu Phe
385                 390                 395                 400

Ser Gly Tyr Thr Leu Asn Asp Thr Trp Ala Lys Ile His Phe Ala Ile
                405                 410                 415

Met Phe Val Gly Val Asn Met Thr Phe Phe Pro Gln His Phe Leu Gly
            420                 425                 430

Leu Ser Gly Met Pro Arg Arg Tyr Ser Asp Tyr Pro Asp Ala Tyr Thr
        435                 440                 445

Met Trp Asn Thr Ile Ser Ser Met Gly Ser Phe Ile Ser Leu Thr Ala
    450                 455                 460

Val Met Leu Met Val Phe Ile Ile Trp Glu Ala Phe Ala Ser Lys Arg
465                 470                 475                 480

Glu Val Leu Thr Val Asp Leu Thr Thr Thr Asn Leu Glu Trp Leu Asn
                485                 490                 495

Gly Cys Pro Pro Tyr His Thr Phe Glu Glu Pro Thr Tyr Val Asn
            500                 505                 510

Leu Lys

<210> SEQ ID NO 22
<211> LENGTH: 297
<212> TYPE: PRT
<213> ORGANISM: Paracoccus denitrificans

<400> SEQUENCE: 22

Met Ala Ile Ala Thr Lys Arg Arg Gly Val Ala Val Met Ser Leu
1               5                   10                  15

Gly Val Ala Thr Met Thr Ala Val Pro Ala Leu Ala Gln Asp Val Leu
                20                  25                  30

Gly Asp Leu Pro Val Ile Gly Lys Pro Val Asn Gly Gly Met Asn Phe
            35                  40                  45

Gln Pro Ala Ser Ser Pro Leu Ala His Asp Gln Trp Leu Asp His
        50                  55                  60

Phe Val Leu Tyr Ile Ile Thr Ala Val Thr Ile Phe Val Cys Leu Leu
65                  70                  75                  80

Leu Leu Ile Cys Ile Val Arg Phe Asn Arg Arg Ala Asn Pro Val Pro
                85                  90                  95

Ala Arg Phe Thr His Asn Thr Pro Ile Glu Val Ile Trp Thr Leu Val
            100                 105                 110

Pro Val Leu Ile Leu Val Ala Ile Gly Ala Phe Ser Leu Pro Ile Leu
        115                 120                 125

Phe Arg Ser Gln Glu Met Pro Asn Asp Pro Asp Leu Val Ile Lys Ala
    130                 135                 140

Ile Gly His Gln Trp Tyr Trp Ser Tyr Glu Tyr Pro Asn Asp Ala Phe
145                 150                 155                 160

Ala Phe Asp Ala Leu Met Leu Glu Lys Glu Ala Leu Ala Asp Ala Gly
                165                 170                 175

Tyr Ser Glu Asp Glu Tyr Leu Leu Ala Thr Asp Asn Pro Val Val Val
            180                 185                 190
```

```
Pro Val Gly Lys Lys Val Leu Val Gln Val Thr Ala Thr Asp Val Ile
        195                 200                 205

His Ala Trp Thr Ile Pro Ala Phe Ala Val Lys Gln Asp Ala Val Pro
    210                 215                 220

Gly Arg Ile Ala Gln Leu Trp Phe Ser Val Asp Gln Glu Gly Val Tyr
225                 230                 235                 240

Phe Gly Gln Cys Ser Glu Leu Cys Gly Ile Asn His Ala Tyr Met Pro
                245                 250                 255

Ile Val Val Lys Ala Val Ser Gln Glu Lys Tyr Glu Ala Trp Leu Ala
                260                 265                 270

Gly Ala Lys Glu Glu Phe Ala Ala Asp Ala Ser Asp Tyr Leu Pro Ala
            275                 280                 285

Ser Pro Val Lys Leu Ala Ser Ala Glu
        290                 295

<210> SEQ ID NO 23
<211> LENGTH: 302
<212> TYPE: PRT
<213> ORGANISM: Rhodobacter sphaeroides

<400> SEQUENCE: 23

Met Arg His Ser Thr Thr Leu Thr Pro Cys Ala Thr Gly Ala Ala Gly
1               5                   10                  15

Leu Leu Ala Ala Thr Ala Ala Ala Gln Gln Thr Leu Glu Ile
            20                  25                  30

Ile Gly Arg Pro Gln Pro Gly Thr Gly Phe His Gly Ser Ala Ser
            35                  40                  45

Pro Val Ala Thr Gln Ile His Trp Leu Asp Gly Phe Ile Leu Val Ile
    50                  55                  60

Ile Gly Ala Ile Thr Ile Phe Val Thr Leu Leu Ile Leu Tyr Ala Val
65                  70                  75                  80

Trp Arg Phe His Glu Lys Arg Asn Lys Val Pro Ala Arg Phe Thr His
                85                  90                  95

Asn Ser Pro Leu Glu Ile Ala Trp Thr Ile Val Pro Ile Val Ile Leu
            100                 105                 110

Val Ala Ile Gly Ala Phe Ser Leu Pro Val Leu Phe Asn Gln Gln Glu
        115                 120                 125

Ile Pro Glu Ala Asp Glu Thr Val Lys Val Thr Gly Tyr Gln Trp Tyr
    130                 135                 140

Trp Gly Tyr Glu Tyr Pro Asp Glu Glu Ile Ser Phe Glu Ser Tyr Met
145                 150                 155                 160

Ile Gly Ser Pro Ala Thr Gly Gly Asp Asn Arg Met Ser Pro Glu Val
                165                 170                 175

Glu Gln Gln Leu Ile Glu Ala Gly Tyr Thr Arg Asp Glu Phe Leu Leu
            180                 185                 190

Ala Thr Asp Thr Ala Met Val Val Pro Val Asn Lys Thr Val Val
        195                 200                 205

Gln Val Thr Gly Ala Asp Val Ile His Ser Trp Thr Val Pro Phe Gly
    210                 215                 220

Val Arg Gln Asp Ala Val Pro Gly Arg Leu Ala Gln Leu Trp Phe Arg
225                 230                 235                 240

Ala Glu Arg Glu Gly Ile Phe Phe Gly Gln Cys Ser Glu Leu Cys Gly
                245                 250                 255

Ile Ser His Ala Tyr Met Pro Ile Thr Val Lys Val Val Ser Glu Glu
            260                 265                 270
```

```
Ala Tyr Ala Ala Trp Leu Glu Gln Ala Arg Gly Gly Thr Tyr Glu Leu
            275                 280                 285

Ser Ser Val Leu Pro Ala Thr Pro Ala Gly Val Ser Val Glu
        290                 295                 300

<210> SEQ ID NO 24
<211> LENGTH: 227
<212> TYPE: PRT
<213> ORGANISM: Bovine (Mitochondria)

<400> SEQUENCE: 24

Met Ala Tyr Pro Met Gln Leu Gly Phe Gln Asp Ala Thr Ser Pro Ile
1               5                   10                  15

Met Glu Glu Leu Leu His Phe His Asp His Thr Leu Met Ile Val Phe
            20                  25                  30

Leu Ile Ser Ser Leu Val Leu Tyr Ile Ile Ser Leu Ile Leu Thr Thr
        35                  40                  45

Lys Leu Thr His Thr Ser Thr Met Asp Pro Gln Glu Val Glu Thr Ile
    50                  55                  60

Trp Thr Ile Leu Pro Ala Ile Ile Leu Ile Leu Ile Ala Leu Pro Ser
65                  70                  75                  80

Leu Arg Ile Leu Tyr Met Met Asp Glu Ile Asn Asn Pro Ser Leu Thr
                85                  90                  95

Val Lys Thr Met Gly His Gln Trp Tyr Trp Ser Tyr Glu Tyr Thr Asp
            100                 105                 110

Tyr Glu Asp Leu Ser Leu Asp Ser Tyr Met Ile Pro Thr Ser Glu Leu
        115                 120                 125

Lys Pro Gly Glu Leu Arg Leu Leu Glu Val Asp Asn Arg Val Val Leu
    130                 135                 140

Pro Met Glu Met Thr Ile Arg Met Leu Val Ser Ser Gly Asp Val Leu
145                 150                 155                 160

His Ser Trp Ala Val Pro Ser Leu Gly Leu Lys Thr Asp Ala Ile Pro
                165                 170                 175

Gly Arg Leu Asn Gln Thr Thr Leu Met Ser Ser Arg Pro Gly Leu Tyr
            180                 185                 190

Tyr Gly Gln Cys Ser Glu Ile Cys Gly Ser Asn His Ser Phe Met Pro
        195                 200                 205

Ile Val Leu Glu Leu Val Pro Leu Lys Tyr Phe Glu Lys Trp Ser Ala
    210                 215                 220

Ser Met Leu
225

<210> SEQ ID NO 25
<211> LENGTH: 56
<212> TYPE: PRT
<213> ORGANISM: G. oxydans DSM 4025 PCR product

<400> SEQUENCE: 25

Gln Phe Thr His Asn Thr Pro Leu Glu Ile Val Trp Thr Ile Val Pro
1               5                   10                  15

Val Val Ile Leu Val Phe Ile Gly Ala Phe Ser Leu Pro Val Leu Phe
            20                  25                  30

Lys Gln Gln Glu Phe Pro Glu Gly Asp Ile Val Ile Asn Val Glu Gly
        35                  40                  45

Arg Ser Trp Tyr Trp Gly Tyr Glu
    50                  55
```

<210> SEQ ID NO 26
<211> LENGTH: 274
<212> TYPE: PRT
<213> ORGANISM: Paracoccus denitrificans

<400> SEQUENCE: 26

```
Met Ala His Val Lys Asn His Asp Tyr Gln Ile Leu Pro Pro Ser Ile
1               5                   10                  15

Trp Pro Phe Phe Gly Ala Ile Gly Ala Phe Val Met Leu Thr Gly Ala
            20                  25                  30

Val Ala Trp Met Lys Gly Ile Thr Phe Phe Gly Leu Pro Val Glu Gly
        35                  40                  45

Pro Trp Met Phe Leu Ile Gly Leu Val Gly Val Leu Tyr Val Met Phe
    50                  55                  60

Gly Trp Trp Ala Asp Val Val Asn Glu Gly Glu Thr Gly Glu His Thr
65                  70                  75                  80

Pro Val Val Arg Ile Gly Leu Gln Tyr Gly Phe Ile Leu Phe Ile Met
                85                  90                  95

Ser Glu Val Met Phe Phe Val Ala Trp Phe Trp Ala Phe Ile Lys Asn
            100                 105                 110

Ala Leu Tyr Pro Met Gly Pro Asp Ser Pro Ile Lys Asp Gly Val Met
        115                 120                 125

Pro Pro Glu Gly Ile Val Thr Phe Asp Pro Trp His Leu Pro Leu Ile
    130                 135                 140

Asn Thr Leu Ile Leu Leu Leu Ser Gly Val Ala Val Thr Trp Ala His
145                 150                 155                 160

His Ala Phe Val Leu Glu Gly Asp Arg Lys Thr Thr Ile Asn Gly Leu
                165                 170                 175

Ile Val Ala Val Ile Leu Gly Val Cys Phe Thr Gly Leu Gln Ala Tyr
            180                 185                 190

Glu Tyr Ser His Ala Ala Phe Gly Leu Ala Asp Thr Val Tyr Ala Gly
        195                 200                 205

Ala Phe Tyr Met Ala Thr Gly Phe His Gly Ala His Val Ile Ile Gly
    210                 215                 220

Thr Ile Phe Leu Phe Val Cys Leu Ile Arg Leu Leu Lys Gly Ala Met
225                 230                 235                 240

Thr Gln Lys Gln His Val Gly Phe Glu Ala Ala Ala Trp Tyr Trp His
                245                 250                 255

Phe Val Asp Val Val Trp Leu Phe Leu Phe Val Val Ile Tyr Ile Trp
            260                 265                 270

Gly Arg
```

<210> SEQ ID NO 27
<211> LENGTH: 266
<212> TYPE: PRT
<213> ORGANISM: Rhodobacter sphaeroides

<400> SEQUENCE: 27

```
Met Ala His Ala Lys Asn His Asp Tyr His Ile Leu Pro Pro Ser Ile
1               5                   10                  15

Trp Pro Phe Met Ala Ser Val Gly Ala Phe Val Met Leu Asn Gly Ala
            20                  25                  30

Val Leu Trp Met His Gly Ser Gly Pro Trp Met Gly Leu Ile Gly Leu
        35                  40                  45
```

```
Val Val Val Leu Tyr Thr Met Phe Gly Trp Trp Ser Asp Val Val Thr
        50                  55                  60
Glu Ser Leu Glu Gly Asp His Thr Pro Val Val Arg Leu Gly Leu Arg
65                  70                  75                  80
Trp Gly Phe Ile Leu Phe Ile Met Ser Glu Val Ile Phe Phe Ser Ala
                85                  90                  95
Trp Phe Trp Ser Phe Phe Lys His Ala Leu Tyr Pro Met Gly Pro Glu
                100                 105                 110
Ser Pro Ile Ile Asp Gly Ile Phe Pro Pro Glu Gly Ile Ile Thr Phe
                115                 120                 125
Asp Pro Trp His Leu Pro Leu Ile Asn Thr Leu Ile Leu Leu Cys Ser
    130                 135                 140
Gly Cys Ala Ala Thr Trp Ala His His Ala Leu Val His Glu Asn Asn
145                 150                 155                 160
Arg Arg Asp Val Ala Trp Gly Leu Ala Leu Ala Ile Ala Leu Gly Ala
                165                 170                 175
Leu Phe Thr Val Phe Gln Ala Tyr Glu Tyr Ser His Ala Ala Phe Gly
                180                 185                 190
Phe Ala Gly Thr Ile Tyr Gly Ala Asn Phe Phe Met Ala Thr Gly Phe
                195                 200                 205
His Gly Phe His Val Ile Val Gly Thr Ile Phe Leu Leu Val Cys Leu
    210                 215                 220
Ile Arg Val Gln Arg Gly His Phe Thr Pro Glu Lys His Val Gly Phe
225                 230                 235                 240
Glu Ala Ala Met Trp Tyr Trp His Phe Val Asp Val Val Trp Leu Phe
                245                 250                 255
Leu Phe Ala Ser Ile Tyr Ile Trp Gly Gln
                260                 265

<210> SEQ ID NO 28
<211> LENGTH: 261
<212> TYPE: PRT
<213> ORGANISM: Bovine (Mitochondria)

<400> SEQUENCE: 28

Met Thr His Gln Thr His Ala Tyr His Met Val Asn Pro Ser Pro Trp
1               5                   10                  15
Pro Leu Thr Gly Ala Leu Ser Ala Leu Leu Met Thr Ser Gly Leu Thr
                20                  25                  30
Met Trp Phe His Phe Asn Ser Met Thr Leu Leu Met Ile Gly Leu Thr
            35                  40                  45
Thr Asn Met Leu Thr Met Tyr Gln Trp Trp Arg Asp Val Ile Arg Glu
50                  55                  60
Ser Thr Phe Gln Gly His His Thr Pro Ala Val Gln Lys Gly Leu Arg
65                  70                  75                  80
Tyr Gly Met Ile Leu Phe Ile Ile Ser Glu Val Leu Phe Phe Thr Gly
                85                  90                  95
Phe Phe Trp Ala Phe Tyr His Ser Ser Leu Ala Pro Thr Pro Glu Leu
                100                 105                 110
Gly Gly Cys Trp Pro Pro Thr Gly Ile His Pro Leu Asn Pro Leu Glu
            115                 120                 125
Val Pro Leu Leu Asn Thr Ser Val Leu Leu Ala Ser Gly Val Ser Ile
    130                 135                 140
Thr Trp Ala His His Ser Leu Met Glu Gly Asp Arg Lys His Met Leu
145                 150                 155                 160
```

```
Gln Ala Leu Phe Ile Thr Ile Thr Leu Gly Val Tyr Phe Thr Leu Leu
                165                 170                 175
Gln Ala Ser Glu Tyr Tyr Glu Ala Pro Phe Thr Ile Ser Asp Gly Val
            180                 185                 190
Tyr Gly Ser Thr Phe Phe Val Ala Thr Gly Phe His Gly Leu His Val
        195                 200                 205
Ile Ile Gly Ser Thr Phe Leu Ile Val Cys Phe Arg Gln Leu Lys
    210                 215                 220
Phe His Phe Thr Ser Asn His His Gly Phe Glu Ala Gly Ala Trp
225                 230                 235                 240
Tyr Trp His Phe Val Asp Val Val Trp Leu Phe Leu Tyr Val Ser Ile
                245                 250                 255
Tyr Trp Trp Gly Ser
            260
```

<210> SEQ ID NO 29
<211> LENGTH: 44
<212> TYPE: PRT
<213> ORGANISM: G. oxydans DSM 4025 PCR product

<400> SEQUENCE: 29

```
Thr Trp Ala His His Ala Ile Val His Gly Asp Arg Lys Lys Thr Ala
1               5                   10                  15
Ile Gly Leu Ala Ile Ala Ile Gly Leu Gly Trp Ile Phe Thr Leu Cys
            20                  25                  30
Gln Ala Tyr Glu Tyr Tyr Glu Ile Val His Thr Glu
        35                  40
```

<210> SEQ ID NO 30
<211> LENGTH: 35
<212> TYPE: PRT
<213> ORGANISM: G. oxydans DSM 4025 PCR product

<400> SEQUENCE: 30

```
Asp Ser Ile Phe Leu Leu Val Cys Leu Ile Arg Ile Leu Arg Gly Ala
1               5                   10                  15
Met Ser Ala Lys Gln His Val Gly Phe Glu Met Ala Ala Trp Tyr Trp
            20                  25                  30
His Phe Val
        35
```

<210> SEQ ID NO 31
<211> LENGTH: 17
<212> TYPE: DNA
<213> ORGANISM: PCR Primer
<220> FEATURE:
<221> NAME/KEY: misc_feature
<222> LOCATION: (1)..(17)
<223> OTHER INFORMATION: n can be either a, t, g, or c.

<400> SEQUENCE: 31
tggttcttcg gncaccc                                                  17

<210> SEQ ID NO 32
<211> LENGTH: 18
<212> TYPE: DNA
<213> ORGANISM: PCR Primer
<220> FEATURE:
<221> NAME/KEY: misc_feature
<222> LOCATION: (1)..(18)
<223> OTHER INFORMATION: n can be a, t, g or c.

```
<400> SEQUENCE: 32
canacccgng tagtatac                                                    18

<210> SEQ ID NO 33
<211> LENGTH: 17
<212> TYPE: DNA
<213> ORGANISM: PCR Primer
<220> FEATURE:
<221> NAME/KEY: misc_feature
<222> LOCATION: (1)..(17)
<223> OTHER INFORMATION: n can be a, t, g or c.

<400> SEQUENCE: 33
caatttacnc ataatac                                                     17

<210> SEQ ID NO 34
<211> LENGTH: 20
<212> TYPE: DNA
<213> ORGANISM: PCR Primer
<220> FEATURE:
<221> NAME/KEY: misc_feature
<222> LOCATION: (1)..(20)
<223> OTHER INFORMATION: n can be a, t, g or c.

<400> SEQUENCE: 34
accataaccc cnatacttat                                                  20

<210> SEQ ID NO 35
<211> LENGTH: 17
<212> TYPE: DNA
<213> ORGANISM: PCR Primer
<220> FEATURE:
<221> NAME/KEY: misc_feature
<222> LOCATION: (1)..(17)
<223> OTHER INFORMATION: n can be a, t, g or c.

<400> SEQUENCE: 35
cantgggcnc atcatgc                                                     17

<210> SEQ ID NO 36
<211> LENGTH: 20
<212> TYPE: DNA
<213> ORGANISM: PCR Primer
<220> FEATURE:
<221> NAME/KEY: misc_feature
<222> LOCATION: (1)..(20)
<223> OTHER INFORMATION: n can be a, t, g or c.

<400> SEQUENCE: 36
accataaccg taaaacanct                                                  20
```

CYTOCHROME C OXIDASE ENZYME COMPLEX

This application is a divisional of U.S. patent application Ser. No. 09/712,768, filed Nov. 14, 2000, which issued as U.S. Pat. No. 6,869,785.

FIELD OF THE INVENTION

The present invention relates to the production of a cytochrome c oxidase complex having cytochrome c oxidase activity. More particularly, present invention relates to recombinant production of 2-keto-L-gulonic acid and biologically useful materials thereof.

BACKGROUND OF THE INVENTION

Cytochrome c oxidase (cytochrome aa3; EC 1.9.3.1) is a terminal oxidase enzyme in the aerobic respiratory electron transport system of mitochondria and many bacteria. The enzyme is a cytoplasmic membrane spanning complex that catalyzes the final step in electron excretion involving the re-oxidation of ferrocytochrome c (electron donor) at the periplasmic surface and the reduction of molecular oxygen (electron acceptor) to water at the cytoplasmic surface. The reaction is coupled to the extrusion of protons across the membrane. This coupling is indispensable for the conservation of biological energy derived from substrate oxidation.

Various types of cytochrome complex, e.g. aa3, a1, caa3, o, bo, co, and bd-types, have been identified as functional terminal oxidases. The purification and characterization of some terminal oxidases has been reported. Matsushita et al. reported that *Acetobacter aceti* IFO 3283 contains two terminal oxidases, cytochrome a1 and o. (Proc. Natl. Acad. Sci., USA, 87: 9863, 1990; J. Bacteriol. 174: 122, 1992). (Id.) Matsushita et al. purified and characterized the cytochrome a1. Matsushita et al. also reported the purification of cytochrome o from *Gluconobacter* (Biochem. Biophys. Acta, 894: 304, 1987). Tayama et al. disclosed the terminal oxidase (cytochrome a1) genes of *A. aceti* (JP 93-317054) and they also purified the oxidase enzyme consisting of four subunits of 72, 34, 21, and 13 kDa and also containing heme a and heme b. The oxidases in *Acetobacter* and *Gluconobacter* belong to quinol oxidase family of oxidases. Cytochrome aa3 (cytochrome c oxidase) has been purified from bovine heart, yeast, and many bacteria including *Paracoccous denitrificans* (Solioz et al., J. Biol. Chem., 257: 1579-1582, 1982) and *Rhodobacter sphaeroides* (Hosler et al., J. Biol. Chem., 267: 24264-24272, 1992).

Mammalian (mitochondrial) cytochrome c oxidase (aa3-type) complex contains 13 different subunits; the three core subunits I, II and III (CO I, II and III) are encoded by mitochondria DNA, while the remaining 10 subunits originate from the nucleus. Bacterial aa3-type cytochrome c oxidase also contains three core subunits that are homologous to the mitochondrial core subunits. However, it is reported that CO III was easily lost during purification, resulting in preparations composed of CO I and CO II only (Ludwig et al., Proc. Natl. Acad. Sci. USA, 77: 196-200, 1980). The cytochrome c oxidase complex consisting of the two-subunit (CO I and II) showed redox activity along with the generation of an electrochemical proton gradient. In the case of *P. denitrificans* (Haltia et al., The EMBO Journal, 10: 2015-2021, 1991) and *R. sphaeroides* (Cao et al., Gene, 101: 133-137, 1991), both two-subunit-type (CO I/II) and three-subunit-type (CO I/II/III) complexes were isolated by different purification methods. Genetically, genes for CO II and III are located in an operon, while the gene for CO I is independently located (Raitio et al., The EMBO Journal, 9: 2825-2833, 1987; Shapleigh et al., Proc. Natl. Acad. Sci. USA, 89: 4786-4790, 1992).

Terminal oxidases, as described above play an important role in cellular growth under aerobic conditions by accomplishing the reduction of the molecular oxygen. In oxidative fermentation, the respiratory chain, including the terminal oxidase, function by completing oxidation of a substrate to produce an oxidized product. In this context, it is very important to improve the efficiency of the respiratory chain in order to achieve efficient oxidative fermentation.

*G. oxydans* DSM 4025 produces 2-keto-L-gulonic acid (hereinafter: 2KGA), an important intermediate in the process of L-ascorbic acid production from L-sorbose via L-sorbosone (T. Hoshino et al., EP 0 366 922 A). The oxidation of the substrate, L-sorbose, to 2KGA was thought to be accomplished by the respiratory electron transport chain. The terminal oxidase that catalyzes the final electron excretion step via oxygen, might be one of the kinetic rate-limiting steps in the 2KGA production system as well as in the production of other redox components. The primary dehydrogenase responsible for 2KGA formation from L-sorbose was isolated (T. Hoshino et al., EP 606621 A) and the genes were cloned and sequenced. Four isozymes of the primary dehydrogenase were found (T. Hoshino et al., EP 832974 A). Their direct electron acceptor, cytochrome c551, was also purified and its gene cloned (T. Hoshino et al., EP 0869175 A). However, the terminal oxidase was not isolated and its genes were not cloned.

SUMMARY OF THE INVENTION

The present invention is aimed at providing the materials for improving the quantity and quality of cytochrome c oxidase, and at improving oxidative fermentation completed by the cytochrome c oxidase by making novel cytochrome c oxidase genes available. The microorganism deposited as *Gluconobacter oxydans* under the accession No. DSM 4025 is the preferred source for providing the novel cytochrome c oxidase and the respective genetic materials of the present invention.

The present invention provides a novel cytochrome c oxidase enzyme complex that is isolated from a natural source or is prepared with the aid of genetic engineering. Such an enzyme complex having cytochrome c oxidase activity is obtainable or obtained from biological or genetic material originated from the microorganism identified as *G. oxydans* DSM 4025 or biologically and/or taxonomically homogeneous cultures of a microorganism having the identifying characteristics of *G. oxydans* DSM 4025. Thus, the present invention provides a novel cytochrome c oxidase complex that is useful as an essential component mediating electron transfer in the respiratory chain.

The cytochrome c oxidase complex exemplified herein display the following physicochemical properties: (i) the presence of at least two core subunits of I (COI) and II (COII), wherein the apparent molecular mass of COI is about 43+/−10 kDa by SDS-PAGE analysis, and apparent molecular mass of COII is about 36+/−10 kDa by SDS-PAGE analysis; and (ii) the absorption spectrum showing aa3-type cytochrome c oxidase displays a 605+/−1 nm peak in reduced minus oxidized difference spectrum. Such a cytochrome c oxidase complex can be provided as a substantially homogeneous isolate derived from the culture of a microorganism identified as *G. oxydans* DSM 4025 or the biologically and/or taxonomically homogeneous cultures of a microorganism having the identifying characteristics of G. oxydans DSM 4025.

The novel cytochrome c oxidase complex of the present invention can be also provided in the form of a recombinant enzyme, which may include a recombinant polypeptide as a core subunit I (COI), wherein the recombinant polypeptide is selected from the group of polypeptides having an amino acid sequence identified by SEQ ID NO:2, and those having amino acid sequences having 85% or higher identity with the sequence and which provides the complex with cytochrome c oxidase activity. Further, the other core subunit II (COII) and III (COIII) may be recombinant polypeptide(s) selected from the group of those containing amino acid sequences identified by SEQ ID NOs: 4, 6 and/or 8 and those containing amino acid sequences having 85% or higher identity with any one of the SEQ ID Nos: 4, 6 and 8, and that provide the complex with cytochrome c oxidase activity.

Another aspect of the present invention are the respective core subunits, i.e. COI, COII and COIII, that are recombinant polypeptides useful as components of the novel cytochrome c oxidase complex of the present invention.

Exemplified herein as COI is a recombinant polypeptide which is a component of the cytochrome c oxidase complex, the polypeptide having an amino acid sequence identified by SEQ ID NO: 2, or an amino acid sequence having 85% or higher identity with the SEQ ID NO:2 and that provides the complex with cytochrome c oxidase activity. The recombinant COI may be a polypeptide capable of providing the complex of the present invention with cytochrome c oxidase activity, and that is encoded by a recombinant DNA fragment containing a DNA sequence selected from the group of:
  (a) the DNA sequence identified by SEQ ID NO: 1, and
  (b) DNA sequences that encode polypeptides having an amino acid sequence identified by SEQ ID NO: 2 or amino acid sequences having 85% or higher identity with SEQ ID NO:2.

Also exemplified herein as COII is a recombinant polypeptide which is a component of the cytochrome c oxidase complex of the present invention, the polypeptide having an amino acid sequence identified by SEQ ID NO: 4, or an amino acid sequence having 85% or higher identity with the amino acid sequence and that is capable of providing the complex with cytochrome c oxidase activity. The recombinant COII may be a polypeptide capable of providing the complex of the present invention with cytochrome c oxidase activity, and that is encoded by a recombinant DNA fragment containing a DNA sequence selected from the group of:
  (a) the DNA sequence identified by SEQ ID NO: 3, and
  (b) the DNA sequences that encode polypeptides having an amino acid sequence identified by SEQ ID NO: 4 or an amino acid sequence having 85% or higher identity with SEQ ID NO:4.

Moreover, exemplified herein as COIII is a recombinant polypeptide that is a component of the cytochrome c oxidase complex of the present invention. Such recombinant polypeptide contains either, or both of the amino acid sequences identified by SEQ ID NOs: 6 and 8, respectively or amino acid sequences having 85% or higher identity with SEQ ID NOs: 6 and 8 and that provide the complex with cytochrome c oxidase activity. The recombinant COIII may be a recombinant polypeptide capable of providing the complex of the present invention with cytochrome c oxidase activity, that is encoded by a recombinant DNA fragment containing one or more DNA sequence(s) selected from the group of:
  (a) the DNA sequence identified by SEQ ID NO: 5,
  (b) the DNA sequence identified by SEQ ID NO: 7,
  (c) the DNA sequences that encode polypeptides having an amino acid sequence identified by SEQ ID NO: 6 or amino acid sequences having 85% or higher identity with the SEQ ID NO:6, and
  (d) the DNA sequences that encode polypeptides having an amino acid sequence identified by SEQ ID NO: 8 or amino acid sequences having 85% or higher identity with SEQ ID NO:8.

Further aspects of the present invention are recombinant DNA fragments useful for preparing the respective core subunits, i.e. COI, COII and COIII by genetic engineering. Such recombinant polypeptides are useful as components of the novel cytochrome c oxidase complex of the present invention. As explained above, these polypeptides should be capable of providing the cytochrome c oxidase complex of the present invention with cytochrome c oxidase activity.

Exemplified herein as a recombinant DNA fragment for COI is a DNA fragment which encodes a polypeptide involved in the cytochrome c oxidase complex, and that includes a DNA sequence selected from the group of:
  (a) the DNA sequence identified by SEQ ID NO: 1, and
  (b) DNA sequences that encode polypeptides having an amino acid sequence identified by SEQ ID NO: 2 or amino acid sequences having 85% or higher identity with SEQ ID NO:2.

Also exemplified herein as a recombinant DNA fragment for COII is a DNA fragment that encodes a polypeptide involved in the cytochrome c oxidase complex and that contains a DNA sequence selected from the group of:
  (a) the DNA sequence identified by SEQ ID NO: 3, and
  (b) DNA sequences that encode polypeptides having an amino acid sequence identified by SEQ ID NO: 4 or amino acid sequences having 85% or higher identity with SEQ ID NO:4.

Also exemplified herein as a recombinant DNA fragment for COIII is a DNA fragment that encodes a polypeptide involved in the cytochrome c oxidase complex and that contains one or more DNA sequence(s) selected from the group of:
  (a) the DNA sequence identified by SEQ ID NO: 5,
  (b) the DNA sequence identified by SEQ ID NO: 7,
  (c) DNA sequences that encode polypeptides having an amino acid sequence identified by SEQ ID NO: 6 or amino acid sequences having 85% or higher identity with SEQ ID NO:6, and
  (d) DNA sequences that encode polypeptides having an amino acid sequence identified by SEQ ID NO: 8 or amino acid sequences having 85% or higher identity with SEQ ID NO:8.

Another aspect of this invention is an expression vector containing one or more of the above mentioned recombinant DNA fragments, the vector being suitable for expression in an organism, including both prokaryotic and/or eukaryotic host cells.

Further, another aspect of the present invention is a recombinant organism into which has been introduced the expression vector mentioned above. Such a recombinant organism is useful for the genetic preparation of the recombinant cytochrome c oxidase complex and also applicable to a process for producing 2KGA from L-sorbose or D-sorbitol in an appropriate culture medium. Host cells for the recombinant organism of the present invention may be of eukaryotic origin, preferably a mammalian or plant cell, or may be of prokaryotic origin. These host cells may in particular be obtained from bacteria, preferably G. oxydans DSM 4025 and biologically and/or taxonomically homogeneous cultures of a microorganism having the identifying characteristics of *Gluconobacter oxydans* DSM 4025.

This invention is also directed to a process for producing cytochrome c oxidase, which includes cultivating the recombinant organism of this invention, as mentioned above, particularly the recombinant organism containing a preferred DNA sequence exemplified herein, in an appropriate culture medium and recovering the cytochrome c oxidase from the culture medium.

Further, this invention is also directed to a process for producing 2KGA from L-sorbose or D-sorbitol, which includes cultivating a recombinant organism of the present invention, as mentioned above, in an appropriate culture medium and recovering 2KGA from the culture.

BRIEF DESCRIPTION OF THE DRAWINGS

The following figures are included to further illustrate the present invention together with the detailed description given below.

FIG. 1A shows the spectrum of the oxidized form. FIG. 1B shows the spectrum of the reduced form. FIG. 1C shows the reduced minus oxidized difference spectrum.

FIG. 3 shows an alignment of the partial amino acid sequences of CO I from *G. oxydans* DSM 4025 with ones from other organisms. The sequences shown include a peptide sequence obtained from *G. oxydans* DSM 4025 (SEQ ID NO: 11), on the line labeled G.O./peptide, and an amino acid sequence deduced from the DNA amplified by PCR from *G. oxydans* DSM 4025 (SEQ ID NO: 13), on the line labeled G.O./PCR, as well as amino acid sequences from *Paracoccus denitrificans* (SEQ ID NO: 19), on the lines labeled P.D., *Rhodobacter sphaeroides* (SEQ ID NO: 20), on the lines labeled R.S., and Bovine (Mitochondria) (SEQ ID NO: 21), on the lines labeled B.M.

FIG. 4 shows an alignment of the partial amino acid sequences of CO II from *G. oxydans* DSM 4025 with ones from other organisms. The sequences shown include a peptide sequence obtained from *G. oxydans* DSM 4025 (SEQ ID NO: 14), on the line labeled G.O./peptide, and an amino acid sequence deduced from the DNA amplified by PCR from *G. oxydans* DSM 4025 (SEQ ID NO: 25), on the lines labeled G.O./PCR, as well as amino acid sequences from *Paracoccus denitrificans* (SEQ ID NO: 22), on the lines labeled P.D., *Rhodobacter sphaeroides* (SEQ ID NO: 23), on the lines labeled R.S., and Bovine (Mitochondria) (SEQ ID NO: 24), on the lines labeled B.M.

FIG. 5 shows an alignment of the partial amino acid sequences of CO III from *G. oxydans* DSM 4025 with those from other organisms. The sequences shown include amino acid sequences deduced from the DNA amplified by PCR from *G. oxydans* DSM 4025 (SEQ ID NOs: 29 [on the upper line labeled G.O./PCR] and 30 [on the lower line labeled G.O./PCR]), as well as amino acid sequences from *Paracoccus denitrificans* (SEQ ID NO: 26), on the lines labeled P.D., *Rhodobacter sphaeroides* (SEQ ID NO: 27), on the lines labeled R.S., and Bovine (Mitochondria) (SEQ ID NO: 28), on the lines labeled B.M.

FIG. 6 shows primers for PCR amplification of the partial CO I, II, III genes of the cytochrom c oxidase complex from *G. oxydans* DSM 4025. The sequences shown include the following: the nucleotide sequence of the CO I (A) primer (SEQ ID NO: 31) and its deduced amino acid sequence (SEQ ID NO: 9), above it; the nucleotide sequence of the CO 1 (B) primer (SEQ ID NO: 32) and its deduced amino acid sequence (SEQ ID NO: 10), above it; the nucleotide sequence of the CO II (A) primer (SEQ ID NO: 33) and its deduced amino acid sequence (SEQ ID NO: 15), above it; the nucleotide sequence of the CO II (B) primer (SEQ ID NO: 34) and its deduced amino acid sequence (SEQ ID NO: 16), above it; the nucleotide sequence of the CO III (A) primer (SEQ ID NO: 35) and its deduced amino acid sequence (SEQ ID NO: 17), above it; the nucleotide sequence of the CO III (B) primer (SEQ ID NO: 36) and its deduced amino acid sequence (SEQ ID NO: 18) above it.

FIG. 7 shows the physical maps of the 8.0 kb PstI and 9.3 kb EcoRI fragments containing the "CO I" and "CO II and III" genes, respectively.

FIG. 8 shows the alignment of the complete amino acid sequence of the CO I subunit from *G. oxydans* DSM 4025 (SEQ ID NO: 2), on the lines labeled G.O., with those from other organisms. The sequences from other organisms include those from Bovine (Mitochondria) (SEQ ID NO: 21), on the lines labeled B.M., *Paracoccus denitrificans* (SEQ ID NO: 19), on the lines labeled P.D., and *Rhodobacter sphaeroides* (SEQ ID NO: 20), on the lines labeled R.S.

DETAILED DESCRIPTION OF THE INVENTION

Figure 1:
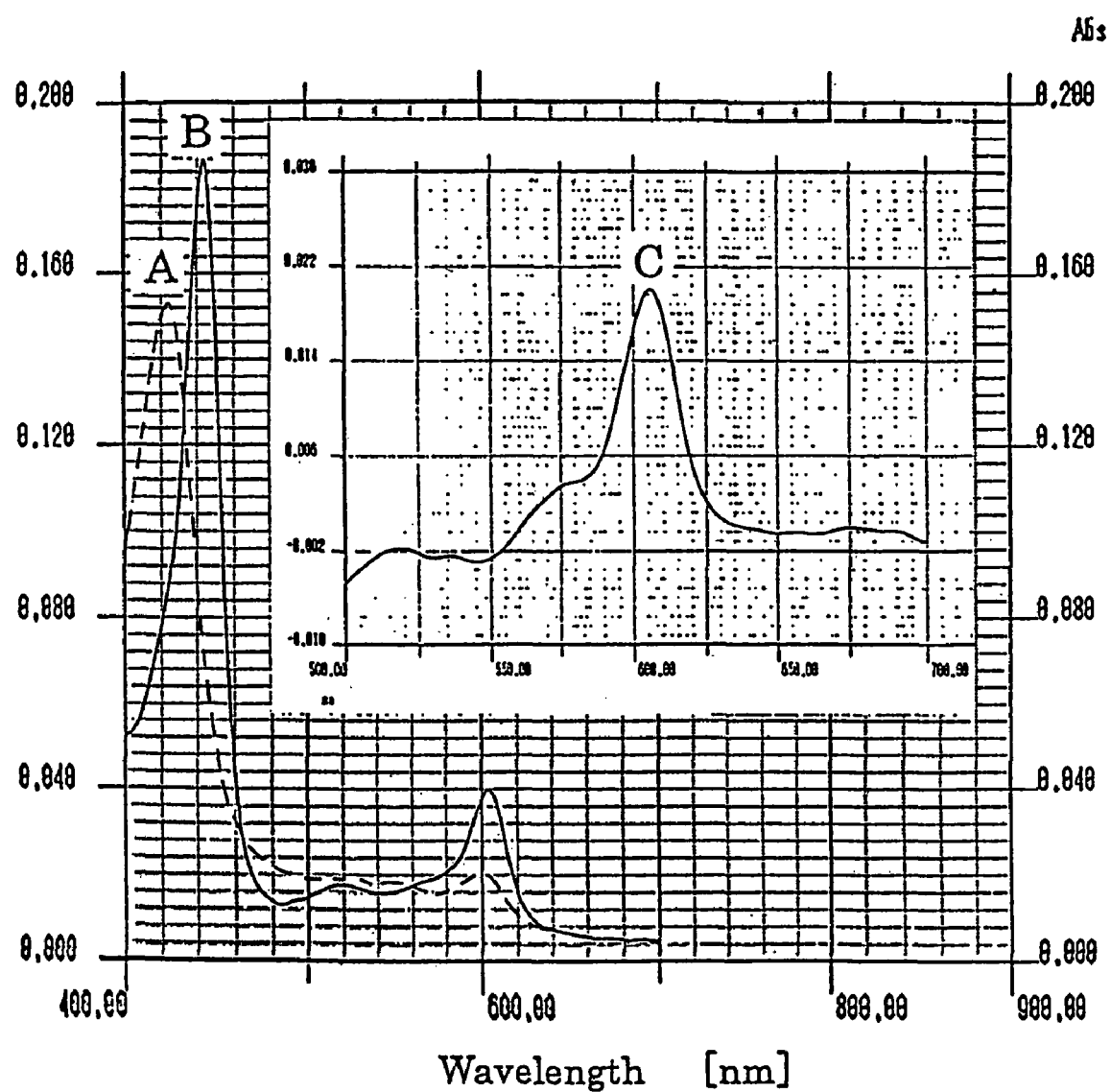
FIG. 1 shows absorption spectra pattern of aa3-type cytochrome c oxidase of *G. oxydans* DSM 4025. Spectra were recorded at room temperature at a protein concentration of 0.08 mg/ml in 25 mM Na-HEPES (pH 7.5) containing 0.5% sucrose monolaurate and 5% glycerol.

The novel cytochrome c oxidase complex of the present invention belongs to a family of proteins, and corresponding genes, that function as a terminal oxidases. More particularly, the novel cytochrome c oxidase of the present invention is useful as a terminal oxidase that oxidizes cytochrome c, an electron acceptor for dehydrogenases, such as alcohol and aldehyde dehydrogenase (AADH), and thus, is useful as an essential component mediating electron transfer in the respiratory chain. The cytochrome c oxidase complex of the present invention may be isolated from a natural source or prepared with the aid of genetic engineering. Such an enzyme complex having cytochrome c oxidase activity is obtainable from biological material originated from a microorganism identified as *G. oxydans* DSM 4025 or biologically and/or taxonomically homogeneous cultures of a microorganism having the identifying characteristics of *G. oxydans* DSM 4025. The cytochrome c oxidase complex of the present invention shows the following physico-chemical characteristics: the complex shows the absorption spectra of aa3-type cytochrome c oxidase in reduced minus oxidized difference spectrum (a peak at 605+/−1 nm) and, two polypeptides involved in the cytochrome c oxidase complex have apparent molecular masses of about 43+/−10 kDa and 36+/−10 kDa on SDS-PAGE.

As used herein, the phrase "a biologically and/or taxonomically homogeneous culture of a microorganism having the identifying characteristics of *G. oxydans* DSM 4025" means a microorganism that has at least 12 out of 14 of the following characteristics of *G. oxydans* DSM 4025:

(a) produces 2-KGA from L-sorbose,
(b) oxidizes ethanol to acetic acid,
(c) oxidizes D-glucose to D-gluconic acid and 2-keto-D-gluconic acid,
(d) exhibits ketogenesis of polyalcohols,
(e) exhibits pellicle and ring growth in mannitol broth (24 hour cultivation) at pH 4 and 5, and pellicle growth in glucose broth at pH 4.5,
(f) does not substantially oxidize glycerol to dihydrooxyacetone,
(g) produces 2-keto-D-glucaric acid from sorbitol and glucaric acid but not from glucose, fructose, gluconic acid, mannitol or 2-keto-D-gluconic acid,
(h) is polymorphic, with no apparent flagella,
(i) produces brown pigment from fructose,
(j) exhibits good growth when co-cultured in the presence of *B. megaterium* or a cell extract thereof,
(k) is streptomycin sensitive,
(l) is rod-shaped with rounded ends,
(m) has an average cell diameter of about 0.3-0.6 micrometers,
(n) has an average cell length of about 1-1.5 micrometers; and which microorganism produces 2-KGA from L-sorbose on the level of at least 0.01 g/L of 2-KGA in the culture medium as measured by HPLC. In addition to this, the phrase "a biologically and/or taxonomically homogeneous culture of a microorganism having the identifying characteristics of *G. oxydans* DSM 4025" should be understood to encompass a microorganism comprising a polynucleotide sequence which hybridizes under high stringency conditions to a polynucleotide sequence which encodes a polypeptide selected from the group consisting of SEQ ID NO:2, 4, 6, and 8, as it is obvious for the person skilled in the art that such a microorganism can be identified based on homology of the amino acid sequences.

The novel recombinant enzyme complex of the present invention can be prepared using genetic material, i.e. recombinant DNA fragments originated from a microorganism identified as *G. oxydans* DSM 4025 or a biologically and/or taxonomically homogeneous cultures of a microorganism having the identifying characteristics of *G. oxydans* DSM 4025. Such a novel cytochrome c oxidase complex may contain at least one recombinant polypeptide as one of the core subunits. The recombinant polypeptide as the core subunit I of the complex may be selected from the group of polypeptides having an amino acid sequence identified by SEQ ID NO: 2 and those amino acid sequences having 85% or higher identity with SEQ ID NO:2 and being capable of providing the complex with cytochrome c oxidase activity. Furthermore, either or both of the other core subunits, II (COII) and III (COIII), may be recombinant polypeptide(s). COII may be selected from the group consisting of recombinant polypeptides containing a partial amino acid sequence identified by SEQ ID NO: 4, and those containing a partial amino acid sequence having 85% or higher identity with SEQ ID NO:4, as long as such recombinant polypeptides are capable of providing the complex with cytochrome c oxidase activity. COIII may be selected from the group of recombinant polypeptides containing partial amino acid sequences identified by SEQ ID NOs: 6 and 8 and those containing partial amino acid sequences having 85% or higher identity with SEQ ID NOs:6 and 8, respectively, as long as such recombinant polypeptides are capable of providing the complex with cytochrome c oxidase activity.

The term "identity" preferably has the meaning that the amino acids occurring at the respective positions are not only similar with regard to their properties, but are in fact identical. In a preferred embodiment the alignment of the amino acid sequences is performed, for example, using the GCG alignment program in Best Fit.

As used herein, % homology data are generated using the "Search Homology" program of Genetyx-SV/RC version 3.2.0 (Genetyx Software Development Co. Ltd., Tokyo, Japan).

The present invention is also directed to the polypeptides involved in the cytochrome c oxidase complex. The polypeptides involved in the cytochrome c oxidase complex and the amino acid sequences described in SEQ ID NOs: 2, 4, 6 and 8 displayed homologies of 50-82%, at most, with the polypeptides or the corresponding partial amino acid sequences, involved in other cytochrome oxidases. For example, the CO I polypeptide of the present invention (SEQ ID NO: 2) displayed 77%, 81% and 79% homology with CO I alpha (accession No. P08305), CO I beta (accession No. P98002) from *P. denitrificans* and CO I from *R. sphaeroides* (accession No. P33517), respectively. The partial CO II polypeptide of the present invention (SEQ ID NO: 4) displayed 73% and 68% homology with the CO II polypeptides from *P. denitrificans* and *R. sphaeroides*, respectively. One of the partial CO III polypeptides of the present invention (SEQ ID NO: 6) displayed 54% homology with the CO III polypeptide from *P. denitrificans* and another polypeptide (SEQ ID NO: 8) displayed 71% and 63% homology with the CO III polypeptides from *P. denitrificans* and *R. sphaeroides*, respectively. These homology searches can be done by a computer program such as "Search Homology" of Genetyx-SV/RC version 3.2.0 (Genetyx Software Development Co. Ltd., Tokyo Japan).

Thus the respective core subunits, i.e. COI, COII and COIII may be provided as recombinant polypeptides which are useful as components of the novel cytochrome c oxidase complex of the present invention.

The subunit COI of the complex may be a recombinant polypeptide which is a component of the cytochrome c oxidase complex of the present invention, the polypeptide having an amino acid sequence identified by SEQ ID NO: 2 or an amino acid sequence having 85% or higher identity with SEQ ID NO:2, and that is capable of providing the complex with cytochrome c oxidase activity, as described above. The recombinant COI may also be a polypeptide that provides the complex of the present invention with cytochrome c oxidase activity, and that is encoded by a recombinant DNA fragment comprising a DNA sequence selected from the group consisting of:

(a) the DNA sequence identified by SEQ ID NO: 1, and
(b) DNA sequences which encode polypeptides having an amino acid sequence identified by SEQ ID NO: 2 or amino acid sequences having 85% or higher identity with SEQ ID NO:2.

Also, the subunit COII may be a recombinant polypeptide which is a component of the cytochrome c oxidase complex of the present invention, the polypeptide having an amino acid sequence identified by SEQ ID NO: 4, or an amino acid sequence having 85% or higher identity with SEQ ID NO:4, and that provides the complex with cytochrome c oxidase activity, as described above. A recombinant COII may also be a polypeptide that provides the complex of the present invention with cytochrome c oxidase activity, and that is encoded by a recombinant DNA fragment containing a DNA sequence selected from the group of:
(a) the DNA sequence identified by SEQ ID NO: 3, and
(b) DNA sequences which encode polypeptides having an amino acid sequence identified by SEQ ID NO: 4 or amino acid sequences having 85% or higher identity with SEQ ID NO:4.

The subunit COIII may be a recombinant polypeptide which is a component of the cytochrome c oxidase complex of the present invention, the polypeptide having either or both of the amino acid sequences identified by SEQ ID NOs: 6 and 8, respectively, or amino acid sequences having 85% or higher identity with SEQ ID NOs: 6 and 8, respectively, as long as such recombinant polypeptides provide the complex with cytochrome c oxidase activity, as described above. A recombinant COIII may also be a recombinant polypeptide capable of providing the complex of the present invention with cytochrome c oxidase activity, that is encoded by a recombinant DNA fragment containing one or more DNA sequence(s) selected from the group of:
(a) the DNA sequence identified by SEQ ID NO: 5,
(b) the DNA sequence identified by SEQ ID NO: 7,
(c) DNA sequences which encode polypeptides having an amino acid sequence identified by SEQ ID NO: 6 or amino acid sequences having 85% or higher identity with SEQ ID NO:6, and
(d) DNA sequences which encode polypeptides having an amino acid sequence identified by SEQ ID NO: 8 or amino acid sequences having 85% or higher identity with SEQ ID NO:8.

The present invention also encompasses functional derivatives of the recombinant polypeptides described above. As used herein, "functional derivatives" are defined, on the basis of the amino acid sequence of the present invention, by addition, insertion, deletion and/or substitution of one or more amino acid residues of such sequences, such as from 1 to 20 exchanges, for example from 2 to 10, 3-5, or 2-3 exchanges, where the cytochrome c oxidase complex including such derivatives still have cytochrome c oxidase activity measured by an assay known in the art or specifically described herein. Such functional derivatives may be made either by chemical peptide synthesis or chemical modification of protein known in the art, or by recombinant means on the basis of the DNA sequences as disclosed herein, by methods known in the state of the art and disclosed, e.g. by Sambrook et al (supra) ("Molecular Cloning" second edition, Cold Spring Harbour Laboratory Press 1989, New York). Amino acid exchanges in proteins and peptides which do not generally alter the activity of such molecules are known in the state of the art and are described, for example, by H. Neurath and R. L. Hill in "The Proteins" (Academic Press, New York, 1979, see especially FIG. 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, as well as these in reverse.

The present invention is directed to recombinant DNA fragments that encode recombinant polypeptides involved in the cytochrome c oxidase complex that is one of the essential components mediating electron transfer in the respiratory chain.

The recombinant DNA fragments which are useful for preparing the respective core subunits, i.e. COI, COII and COIII, by genetic engineering are provided. Such recombinant polypeptides are useful as components of the novel cytochrome c oxidase complex of the present invention.

A recombinant DNA fragment for COI may be a DNA fragment that encodes a polypeptide involved in the cytochrome c oxidase complex and that includes a DNA sequence selected from the group of:
(a) the DNA sequence identified by SEQ ID NO: 1, and
(b) DNA sequences which encode polypeptides having an amino acid sequence identified by SEQ ID NO: 2, or amino acid sequences having 85% or higher identity with SEQ ID NO:2.

A recombinant DNA fragment for COII may be a DNA fragment which encodes a polypeptide involved in the cytochrome c oxidase complex and that contains a DNA sequence selected from the group of:
(a) the DNA sequence identified by SEQ ID NO: 3, and
(b) DNA sequences which encode polypeptides having an amino acid sequence identified by SEQ ID NO: 4, or amino acid sequences having 85% or higher identity with SEQ ID NO:4.

A recombinant DNA fragment for COIII may be a DNA fragment which encodes a polypeptide involved in cytochrome c oxidase complex and contains one or more DNA sequence(s) selected from the group of:
(a) the DNA sequence identified by SEQ ID NO: 5,
(b) the DNA sequence identified by SEQ ID NO: 7,
(c) DNA sequences which encode polypeptides having an amino acid sequence identified by SEQ ID NO: 6, or amino acid sequences having 85% or higher identity with SEQ ID NO:6, and
(d) DNA sequences which encode polypeptides having an amino acid sequence identified by SEQ ID NO: 8, or amino acid sequences having 85% or higher identity with SEQ ID NO:8.

The recombinant DNA fragment of this invention may also include a DNA sequence which is capable of hybridizing to SEQ ID NO: 1, 3, 5, or 7 under standard stringency conditions which are described in more detail below.

As used herein the phrase "standard conditions for hybridization" means conditions which are generally used by a person skilled in the art to detect specific hybridization signals and which are described, e.g. by Sambrook et al (supra), or preferably, so called stringent hybridization and non-stringent washing conditions, or more preferably, so called moderately stringent conditions, or even more preferably, so called stringent hybridization and stringent washing conditions which a person skilled in the art is familiar with and which are described, e.g. in Sambrook et al (supra).

For example, any combination of the following hybridization and wash conditions may be used, as appropriate:

High Stringency Hybridization:
6×SSC
0.5% SDS
100 ug/ml denatured salmon sperm DNA
50% formamide
Incubate overnight with gentle rocking at 42° C. overnight.

High Stringency Wash:
1 wash in 2×SSC, 0.5% SDS at Room Temperature for 15 minutes,
followed by another wash in 0.1×SSC, 0.5% SDS at Room Temperature for 15 minutes.

Low Stringency Hybridization:
6×SSC
0.5% SDS
100 ug/ml denatured salmon sperm DNA
50% formamide
Incubate overnight with gentle rocking at 37° C. overnight.

Low Stringency Wash:
1 wash in 0.1×SSC, 0.5% SDS at Room Temperature for 15 minutes.

Moderately stringent conditions may be obtained by varying the temperature at which the hybridization reaction occurs and/or the wash conditions as set forth above.

The present invention also provides an expression vector containing one or more of the above mentioned recombinant DNA fragments. The vector is suitable for the expression in an organism, including both prokaryotic- or eukaryotic host cells. Such an expression vector is constructed by inserting one or more of the above mentioned recombinant DNA fragments into a suitable vector which may carry expression control elements, as is well known in the art. As used herein, expression control elements include enhancers and cis elements to which trans-acting factors bind to control gene expression.

Further, a recombinant organism of the present invention may be prepared by introducing an expression vector mentioned above to an appropriate host cell. Such a recombinant organism of the invention would be useful for the genetic preparation of the recombinant cytochrome c oxidase complex of the present invention and also applicable to a process for producing 2KGA from L-sorbose or D-sorbitol in an appropriate culture medium. Host cells for the recombinant organism of the present invention may be of eukaryotic origin, preferably a mammalian or plant cell, or may be of prokaryotic origin. These host cells may in particular be obtained from bacteria, preferably *G. oxydans* DSM No. 4025 and biologically and/or taxonomically homogeneous cultures of a microorganism having the identifying characteristics of *G. oxydans* DSM 4025. Host cells may also be selected from the group consisting of bacteria, such as *Escherichia coli, Pseudomonas putida, Acetobacter xylinum, Acetobacter pasteurianus, Acetobacter aceti, Acetobacter hansenii*, and *G. oxydans*.

In addition, the present invention also provides a process for producing cytochrome c oxidase. This process includes cultivating a recombinant host cell, as defined above, in an appropriate culture medium and recovering the cytochrome c oxidase from the culture.

The cytochrome c oxidase complex of the present invention is also used for improving 2KGA production from L-sorbose or D-sorbitol and also in the production of aldehydes, carboxylic acids, and ketones from corresponding substrates in the presence of alcohol and aldehyde dehydrogenase in vivo and in vitro.

The compound 2KGA is an important intermediate for the production of L-ascorbic. The production of 2KGA from L-sorbose, or from D-sorbitol by fermentation is known (T. Hoshino et al., EP 88116156 A). *Gluconobacter* strains are known to produce 2KGA via the reaction catalyzed by sorbose and sorbosone dehydrogenases as disclosed in Agric. Biol. Chem., 54(5), 1211-1218, 1990 (T. Hoshino et al.) and in EP 606621 A (T. Hoshino et al.). The genes of primary dehydrogenases responsible for 2KGA formation from L-sorbose or D-sorbitol have been isolated (T. Hoshino et al., EP 832974 A). Furthermore, the cytochrome c that functions as an electron acceptor of the primary dehydrogenases as well as its gene have also been isolated (T. Hoshino et al., EP 869175 A). These dehydrogenases and cytochrome c have been used to produce 2KGA in vitro. The genes have been used to construct recombinant organisms producing 2KGA from L-sorbose and D-sorbitol; e.g. *Pseudomonas putida* carrying the genes of alcohol/aldehyde dehydrogenase (AADH) together with cytochrome c can produce 2KGA from L-sorbose.

Therefore, the present invention includes the use of the cytochrome c oxidase set forth above for the production of 2KGA.

The terminal oxidase activity of the present cytochrome c oxidase complex was spectrophotometrically measured using TMPD (N,N,N',N'-tetramethyl-p-phenylenediamine dihydrochloride) as an artificial substrate (electron donor). The reaction mixture consists of 2.5 mM TMPD, 0.05% Tween-20 and 0.1 M sodium 3[N-morpholino]propanesulfonic acid (Na-MOPS) (pH 6.5). The TMPD oxidase activity can be measured by increasing of absorption at 520 nm with the mole coefficient of TMPD taken as 6.1/mM/cm. One unit of enzyme activity is defined as 1 micromole oxidation of TMPD per one minute at room temperature.

Spectrophotometric identification and quantification of a-type heme were carried out by detection of the characteristic positive peak around 605 nm by reduced minus oxidized difference spectrum. Reduction of each sample was carried out by the addition of a tiny amount of sodium dithionite and by oxidation with ammonium persulfate. The mole coefficient of the a-type heme peak (605 nm-630 nm) was taken as 11.7/mM/cm.

Before describing the present invention in more detail the physico-chemical properties of purified cytochrome c oxidase consisting of subunits, CO I and CO II, as obtainable from *G. oxydans* DSM 4025 are given below.

(1) Absorption Spectrum

The absorption profile of the cytochrome c oxidase complex in reduced minus oxidized difference spectra is shown in FIG. 1.

(2) Molecular Weight

Figure 2:
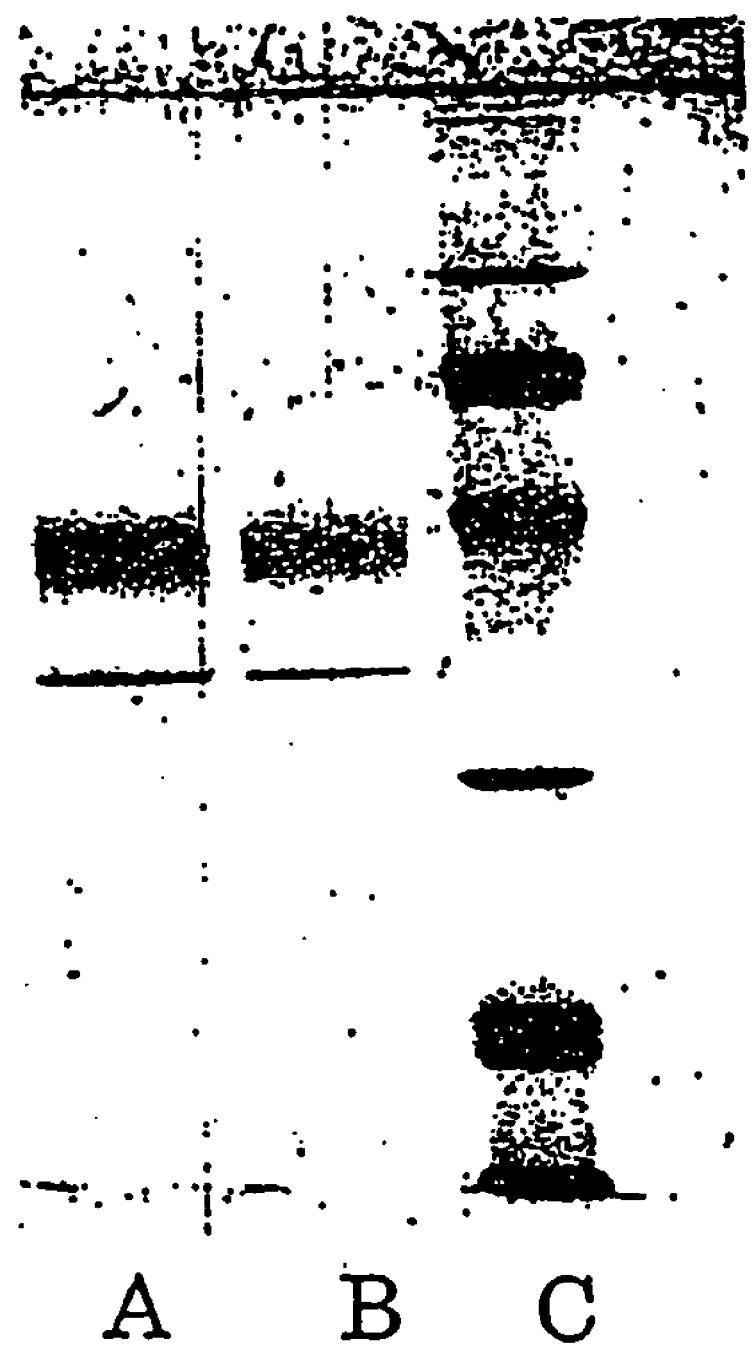
FIG. 2 shows SDS-PAGE analysis of the purified cytochrome c oxidase aa3 of *G. oxydans* DSM 4025. The purified enzyme (at a protein concentration of 0.5 mg/ml) was denatured by incubation with 2% SDS, 50 mM dithioerythritol, 62.5 mM Tris-HCl (pH 6.8) and 10% glycerol at 37° C. for 5 hours. Electrophoresis was carried out at 12.5% acrylamide concentration according to the method of Laemmli (Nature, 227: 680-685, 1970) with the buffer consisting of 25 mM Tris, 0.192 M glycine, and 0.1% SDS. Lane A and B contain 6 microgram and 3 microgram of the purified enzyme, respectively. Lane C contains low range prestained SDS-PAGE standards (Bio-Rad Laboratories, CA U.S.A.).

SDS-PAGE analysis indicated apparent molecular masses of about 43+/−10 and 36+/−10 kDa for the cytochrome c oxidase CO I and CO II subunits, respectively, as shown in FIG. 2.

(3) Amino Acid Sequences of the CO I and CO II

The cytochrome c oxidase complex purified was dissociated into CO I and II subunits by a preparative-disc-SDS-PAGE (NA-1800, Nippon Eido Co.). Both N-terminal alpha-amino residues were blocked by unidentified modification. Partially digested peptide fragments (15-45 kDa MW.) were then obtained by lysyl-endopeptidase treatment, isolated by band extraction from a 15% SDS-PAGE sheet, washed in a Centricon-10 (Amicon) with 15% methanol and 0.1% SDS, and applied to the sequencer. "KDIGLLYLVAAGVVGF" (SEQ ID NO: 11) and "KASQFTHNTPLEIVWTIVPV" (SEQ ID NO: 14) sequences were obtained for CO I and COII, respectively.

The preferred strain used for isolating polypeptides and genes of cytochrome c oxidase of the present invention is the *G. oxydans* strain that deposited at the Deutsche Sammlung von Mikroorganismen in Göttingen (Germany) under DSM 4025 on Mar. 17, 1987 under the stipulations of the Budapest Treaty. Moreover, a subculture of the strain has also been deposited in the Agency of Industrial Science and Technology, Fermentation Research Institute, Japan, under the stipulations of the Budapest Treaty under the deposit No.: *Gluconobacter oxydans* FERM BP-3812 (date of deposit: Mar. 30, 1992). Furthermore, EP 278 447, which is hereby incorporated by reference as if recited in full herein, discloses the characteristics of this strain. Functional equivalents, subcultures, mutants and variants of said microorganism can also be used in the present invention. Biologically or taxonomically homogeneous cultures of a microorganism having the identifying characteristics of the strain DSM 4025 can also be used as the source of the polypeptides and genes of the said cytochrome c oxidase.

The cytochrome c oxidase provided by the present invention may be prepared by cultivating an appropriate organism, disrupting the cells and isolating and purifying it from a cell free extract of disrupted cells, preferably from the soluble fraction of the organism.

The organisms may be cultured in an aqueous medium supplemented with appropriate nutrients under aerobic conditions. The cultivation may be conducted at a pH between about 4.0 and 9.0, preferably between about 6.0 and 8.0. While the cultivation period varies depending upon pH, temperature and nutrient medium used, usually 2 to 6 days will bring about favorable results. A preferred temperature range for carrying out the cultivation is from about 13° to 36° C., preferably from about 18° to 33° C.

It is usually required that the culture medium contains such nutrients as assimilable carbon sources, digestible nitrogen sources and inorganic substances, vitamins, trace elements and the other growth promoting factors. As assimilable carbon sources, glycerol, D-glucose, D-mannitol, D-fructose, D-arabitol, L-sorbose, D-sorbitol and the like can be used.

Various organic or inorganic substances may also be used as nitrogen sources, such as yeast extract, meat extract, peptone, casein, corn steep liquor, urea, amino acids, nitrates, ammonium salts and the like. As inorganic substances, magnesium sulfate, potassium phosphate, ferrous and ferric chlorides, calcium carbonate and the like may be used.

Preferred, embodiments for the isolation and purification of cytochrome c oxidase from the organisms after their cultivation and for the cloning of the gene/DNA sequence are described.

(1) Cells are harvested from fermentation broth by centrifugation or filtration.

(2) The cells are suspended in buffer solution and disrupted by means of a homogenizer, sonicator or treatment with lysozyme and the like, to give a disrupted solution of cells.

(3) Cytochrome c oxidase is isolated and purified from a cell free extract of disrupted cells, preferably from the soluble fraction of the organisms by usual protein purification methods such as ammonium sulfate precipitation, dialysis, ion exchange chromatography, gel filtration chromatography, and affinity chromatography.

The cytochrome c oxidase as provided by the present invention is useful as a terminal oxidase oxidizing cytochrome c that functions as an electron acceptor from a dehydrogenase enzyme in the production of aldehydes, carboxylic acids and ketones from alcohols and aldehydes, especially for the production of 2KGA from L-sorbose or D-sorbitol via L-sorbosone.

Briefly, the cytochrome c oxidase genes, the DNA sequences, the recombinant expression vector and the recombinant organism, also referred to as the transformed host cell, utilized in the present invention can be obtained by the following steps:

(1) Isolating chromosomal DNA from the organisms that can provide the cytochrome c oxidase of the present invention and constructing a gene library of the chromosomal DNA in *Escherichia coli*.

(2) Cloning cytochrome c oxidase genes from chromosomal DNA by colony-, plaque- or Southern-hybridization, PCR (polymerase chain reaction) cloning, Western-blot analysis and the like.

(3) Determining the nucleotide sequences of the cytochrome c oxidase genes obtained as above by utilizing accepted methods to select recombinant DNA fragments containing the cytochrome c oxidase genes constructing an expression vector on which cytochrome c oxidase genes can be efficiently expressed.

(4) Constructing recombinant organisms carrying the cytochrome c oxidase genes by transformation, transduction, transconjugation and electroporation.

The materials and the techniques used in the above aspect of the present invention are exemplified, in detail, as follows:

Total chromosomal DNA may be purified by a procedure well known in the art. The genes encoding cytochrome c oxidase may be cloned in either plasmid or phage vectors from total chromosomal DNA by the following methods:

(i) by determining the partial amino acid sequences of the purified cytochrome c oxidase subunits by isolating the whole protein or peptide fragments, obtained by peptidase-treatment of the gel after SDS-polyacrylamide gel electrophoresis and applying them to a protein sequencer such as Applied Biosystems automatic gas-phase sequencer 470A (Perkin Elmer Corp., Norwalk, Conn., USA), synthesizing oligonucleotide probes with a DNA synthesizer such as Applied Biosystems automatic DNA sequencer 381A (Perkin Elmer), such oligonucleotide probes corresponding to the amino acid sequences obtained as above, isolating clones carrying the objective by utilizing the oligonucleotide probes to perform southern-, colony-, or plaque hybridization on a gene library of the strain carrying the objective genes; (ii) by selecting clones expressing cytochrome c oxidase subunits from the gene library by immunological methods using antibodies against the subunits of cytochrome c oxidase; or (iii) by amplifying the DNAs from the total chromosomal DNA by the PCR method using pairs of oligonucleotides synthesized according to the amino acid sequences determined as above, and isolating clones carrying the whole genes of cytochrome c oxidase subunits from a gene library constructed in *E. coli* by Southern-, colony-, or plaque-hybridization using the PCR product obtained above as the probe. The above-mentioned antibodies that react against the subunits of cytochrome c oxidase may be prepared using the purified proteins of cytochrome c oxidase subunits, or their peptide fragments, by a method such as that described in Methods in Enzymology, vol. 73, p 46, 1981.

The nucleotide sequences of the cytochrome c oxidase genes may be determined by a well-known method, such as the dideoxy chain termination method using M13 phage (Sanger F. et al., Proc. Natl. Acad. Sci. USA, 74:5463-5467, 1977).

To express the genes of cytochrome c oxidase complex subunits, various promoters may be used; for example, the original promoter existing upstream of the genes for cytochrome c oxidase subunits, promoters of antibiotic resistance genes such as the kanamycin resistance gene of Tn5 (Berg, D. E., and C. M. Berg. 1983. Bio/Technology 1: 417-435), the ampicillin resistance gene of pBR322, the beta-galactosidase gene of *E. coli* (lac), the trp-, tac-, and trc-promoters, promoters of lambda phage and any promoters that are functional in a host consisting of organisms including bacteria such as *E. coli, P. putida, A. xylinum, A. pasteurianus, A. aceti, A. hansenii,* and *G. oxydans*, especially *G. oxydans* DSM 4025, mammalian cells and plant cells.

Other regulatory elements may be included, such as a Shine-Dalgarno (SD) sequence (for example, AGGAGG etc., including natural and synthetic sequences operable in the host cell) and a transcriptional terminator (inverted repeat structure including any natural and synthetic sequence operable in the host cell) that are operable in the host cell into which the coding sequence will be introduced and used with the above described promoter.

A wide variety of host/cloning vector combinations may be employed in cloning the double-stranded DNA. The cloning vector is generally a plasmid or phage which contains a replication origin, regulatory elements, a cloning site including a multi-cloning site, and selection markers such as antibiotic resistance genes including resistance genes for ampicillin, tetracycline, kanamycin, streptomycin, gentamicin, spectinomycin etc.

Preferred vectors for the expression of the object gene in *E. coli* are selected from any vectors usually used in *E. coli*, such as pBR322 or its derivatives, including pUC18 and pBluescript II, pACYC177 and pACYC184 (J. Bacteriol., 134: 1141-1156, 1978) and their derivatives, and a vector derived from a broad host range plasmid such as RK2 or RSF1010. A preferred vector for the expression of the subject gene in *Gluconobacter* including *G. oxydans* DSM 4025 and *P. putida*, is selected from any vectors which can replicate in *Gluconobacter* and/or *P. putida*, as well as a in preferred cloning organism such as *E. coli*. The preferred vector is a broad-host-range vector, such as a cosmid vector like pVK102 and its derivatives, and RSF1010 and its derivatives, and a vector containing a replication origin functional in *Gluconobacter* and another origin functional in *E. coli*. The copy number and stability of the vector should be carefully considered for stable and efficient expression of the cloned gene and also for efficient cultivation of the host cell carrying the cloned gene. DNA sequences containing transposable elements such as Tn5 can be also used as a vector to introduce the object gene into the preferred host, especially on the host chromosome. DNA sequences containing any DNAs isolated from the preferred host together with the object gene are also useful to introduce the desired DNA sequence into the preferred host, especially on the host chromosome. Such DNA sequences can be transferred to the preferred host by transformation, transduction, transconjugation or electroporation.

Useful hosts are of prokaryotic or eukaryotic origin and may include organisms, mammalian cells, and plant cells. As a preferable organism, there may be mentioned bacteria such as *E. coli, P. putida, A. xylinum, A. pasteurianus, A. aceti, A. hansenii, G. oxydans*, and any Gram-negative bacteria which are capable of producing recombinant cytochrome c oxidase. Functional equivalents, subcultures, mutants and variants of said organism can be also used in the present invention. A preferred strain is *E. coli* K12 and its derivatives, *P. putida* or *G. oxydans* DSM 4025 and biologically or taxonomically homogeneous cultures of a microorganism having the identifying characteristics of strain DSM 4025.

The DNA sequence encoding cytochrome c oxidase of the present invention is ligated into a suitable vector containing a regulatory region such as a promoter and a ribosomal binding site and transcriptional terminator operable in the host cell described above by well-known methods in the art to produce an expression vector.

To construct a host cell carrying an expression vector, various DNA transfer methods including transformation, transduction, conjugal mating (Chapters 14 and 15, Methods for General and Molecular Bacteriology, Philipp Gerhardt et al. ed., American Society for Microbiology, 1994), and electroporation can be used. The method for constructing a transformed host cell may be selected from the methods well-known in the field of molecular biology. Usual transformation methods can be used for *E. coli, Pseudomonas* and *Acetobacter*. Transduction methods can also be used for *E. coli*. Conjugal mating system can be used in Gram-positive and Gram-negative bacteria including *E. coli, P. putida* and *G. oxydans*. A preferred conjugal mating method was disclosed in WO 89/06688. The conjugation can occur in liquid medium or on a solid surface. The preferred recipient for cytochrome c oxidase production is selected from *E. coli, P. putida* and *G. oxydans*. The preferred recipient for 2KGA production is selected from *E. coli, P. putida* and *G. oxydans*, which can produce active AADHs and cytochrome c with a suitable recombinant expression vector. The preferred recipient for 2KGA production is *G. oxydans* DSM 4025. A selective marker is usually added to the recipient in conjugal mating, for example, resistance against nalidixic acid or rifampicin is usually selected.

The following examples are provided to further illustrate the process of the present invention. These examples are illustrative only and are not intended to limit the scope of the invention in any way.

EXAMPLES

Example 1

Identification and Purification of Cytochrome c Oxidase from *G. oxydans* DSM 4025

Terminal oxidase activity was spectrophotometrically measured using TMPD (N,N,N',N'-tetramethyl-p-phenylenediamine dihydrochloride) as an artificial substrate (electron donor). The reaction mixture consisted of 2.5 mM TMPD, 0.05% Tween-20 and 0.1 M sodium 3[N-morpholino]propanesulfonic acid (Na-MOPS) (pH 6.5). TMPD oxidase activity was measured as an increase in absorption at 520 nm, and the molar coefficient of TMPD was taken as 6.1/mM/cm. One unit of enzyme activity was defined as 1 micromole oxidation of TMPD per one minute at room temperature. Spectrophotometric identification and quantification of a-type heme were carried out by analyzing a reduced minus oxidized difference spectrum to detect the characteristic positive peak around 605 nm. Each sample was reduced with sodium dithionite and oxidized with ammonium persulfate. The molar coefficient of the a-type heme peak (605 nm-630 nm) was taken as 11.7/mM/cm.

*G. oxydans* DSM 4025 was aerobically cultivated in 5 liters of FYC medium, consisting of 10% L-sorbose (sterilized separately), 0.05% glycerol, 1.6% urea (sterilized separately, 0.25% $MgSO_4 \times 7H_2O$, 6.25% baker's yeast cells, 1.5% $CaCO_3$ (production grade, nacalai tesque, Kyoto, Japan), and 3.0% corn steep liquor, pH 7.5 (before sterilization), at 30° C. for 27 hours. After the cultivation, solid materials such as $CaCO_3$ and yeast cells were precipitated by low speed centrifugation (1,000 rpm for 5 minutes) and removed. *G. oxydans* DSM 4025 cells remaining in the culture supernatant were collected by centrifugation at 8,000 rpm for 20 minutes and washed once with 25 mM sodium N-[2-hydroxyethyl] piperazine-N'-[4-butanesulfonic acid] (Na-HEPES) (pH 7.5) containing 0.25 M NaCl, and 2 mM $MgCl_2$.

The resulting cells (about 35 g wet weight) were suspended in about 200 ml of 25 mM Na-HEPES (pH 7.5) containing 0.5 mM ethylenediamine tetraacetic acid (EDTA), 0.5 mM ethylene glycol-bis-beta-aminoethyl ether (EGTA), 0.5 mM phenylmethylsulfonyl fluoride (PMSF), 1 microgram/ml pepstatin A, 1 microgram/ml leupeptin, 10 microgram/ml DNase I and 10 microgram/ml RNase A. The cell suspension was treated with a French press homogenizer at 1500 $kg/cm^2$ twice. The resulting suspension was centrifuged at 10,000 rpm for 10 minutes to remove cell debris, and the supernatant was collected as a cell-free extract (424.0 mg proteins). The cell-free extract was subjected to ultra-centrifugation at 55000 rpm for 1 hour to recover the precipitate as a crude membrane fraction. The crude membrane fraction was resuspended in 50 ml of 25 mM Na-HEPES (pH 7.5) containing 1.2% Tween 20, 0.25 M NaCl, 2 mM $MgCl_2$, 0.5 mM PMSF, 1 microgram/ml pepstatin A, 1 microgram/ml leupeptin and incubated for 1 hour to wash the membrane fraction. The fraction was again subjected to ultra-centrifugation at 55,000 rpm for 1 hour to recover the precipitate as a washed membrane fraction. The washed membrane fraction was incubated with 50 ml of 25 mM Na-HEPES (pH 7.5) containing 1.5% sucrose monolaulate (DOJIN Laboratories, Kumamoto, Japan), 2 mM EDTA and 5% glycerol for 1 hour to solubilize the membrane-bound proteins. The resulting suspension was subjected to ultra-centrifugation at 55,000 rpm for 1 hour to obtain a supernatant (50 ml) as a solubilized membrane fraction. Reduced minus oxidized difference spectrum of the solubilized membrane fraction displayed a characteristic positive peak around 605 nm; the peak corresponded to 0.41 nmoles of a-type heme/mg of crude proteins as content. The membrane-bound proteins in the solubilized membrane fraction were loaded on a DEAE-Toyopearl 650M (TOSOH, Tokyo, Japan) column (ID 2.2×5 cm) which had been equilibrated with 25 mM Na-HEPES containing 0.5% sucrose monolaurate and 5% glycerol. Fractionation was carried out by a linear gradient of 0-0.35 M NaCl in the same buffer. Fractions displaying an a-type heme spectra (positive peak around 605 nm on reduced minus oxidized difference spectrum) and TMPD oxidase activity were eluted at around a 0.28 M concentration of NaCl. These fractions were collected (64 ml), dialyzed against 45 mM potassium phosphate buffer (KPB) (pH 7.6) containing 45 mM NaCl, 5% glycerol and 0.5% sucrose monolaurate, and the enzyme solution was loaded on a hydroxylapatite (TONEN Co., Tokyo, Japan) column (ID 1.5×6 cm) that had been equilibrated with the same buffer. The column was first washed with the same buffer and then with 500 mM KPB (pH 7.6) containing 500 mM NaCl, 5% glycerol and 0.5% sucrose monolaurate. The active fractions were eluted with 900 mM KPB (pH 7.6) containing 900 mM NaCl, 5% glycerol and 0.5% sucrose monolaurate, and collected. The fraction (8.6 mg protein) from the hydroxylapatite column was dialyzed against 25 mM Na-HEPES (pH 7.5) containing 0.5% sucrose monolaurate and 5% glycerol, concentrated by ultrafiltration using YM-30 membrane (Amicon Inc., MA, USA) and stored at −30° C. as a purified protein.

The purified protein was subjected to native-polyacrylamide gel electrophoresis (Native-PAGE) analysis in the presence of 0.5% sucrose monolaurate. The purified protein displayed a visible band with greenish color (without protein staining) which corresponded to a single protein band (with protein staining). The purified protein had 2.6 units/mg of TMPD oxidase activity and displayed the typical absorption spectra pattern of aa3-type cytochrome c oxidase (FIG. 1). The concentration of a-type heme was estimated to be 19.2 nmoles/mg of purified protein. Purification of a-type heme from the washed membrane yielded a 100-fold increase in concentration with nearly 90% recovery. These results indicated that the purified protein was a major component exhibiting TMPD-oxidase activity in *G. oxydans* DSM 4025, and can function as a terminal oxidase in the respiratory system. SDS-PAGE analysis disassociated the purified protein into two protein components: one displayed a broad band with an apparent molecular weight of about 43,000 (named as CO I) and the other displayed a sharp band with an apparent molecular weight of about 36,000 (named as CO II); (FIG. 2).

Example 2

Amino Acid Sequence of the Cytochrome c Oxidase of *G. oxydans* DSM 4025 and the Homologies with the Other Cytochrome c Oxidase Complexes Two components (CO I and CO II) of the purified cytochrome c oxidase of *G. oxydans* DSM 4025 were disassociated by preparative SDS-PAGE. Native N-terminal amino acid sequences were not obtained from either component. To obtain the internal amino acid sequence, each component was digested with lysyl-endopeptidase and the resulting fragments were isolated by preparative SDS-PAGE and subjected to amino acid sequencing with an amino acid sequencer (Applied Biosystems model 470A, The Perkin Elmer Corp., Conn., USA). Consequently, partial amino acid sequences were obtained; KDIGLLYLVAAGVVGF [SEQ ID NO: 11], was obtained from the CO I fragment (slightly lower molecular weight than the original) and KASQFTHNTPLEIVW-TIVPV [SEQ ID NO:14], from the CO II fragment (about a 10000 lower molecular weight than the original). The partial amino acid sequences of the CO I and CO II subunits were compared with the total amino acid sequence of cytochrome c oxidase complexes of *P. denitrificans* and *R. sphaeroides* and bovine mitochondria by sequence-alignments (FIGS. 3 to 4). These strains were chosen because CO I and CO II were similar to those of the cytochrome c oxidase of *P. dentrificans* (B. Ludwig and G. Schatz, Proc. Natl. Acad. Sci. USA, 77, 196-200, 1980) with regards to both their SDS-PAGE and spectrophotometric characteristics. Total homology in the amino acid sequences among three cytochrome c oxidase complexes had been previously reported (C. Jianli et al., J. Biol. Chem., 267, 24273-24278, 1992). As shown in FIGS. 3 and 4, the amino acid sequences of *G. oxydans* DSM 4025 cytochrome c oxidase CO I and CO II were partially assigned to the homology alignment of the others. Especially, significant homology was observed with two bacterial sequences (*P. denitrificans* and *R. sphaeroides*).

Example 3

Cloning of Cytochrome c Oxidase Genes of *G. oxydans* DSM 4025

(1) Amplification of Partial Cytochrome c Oxidase Gene(s) by the PCR Method.

According to the total amino acid sequence alignments of *P. denitrificans, R. sphaeroides* and bovine mitochondria together with the amino acid sequences of the purified CO I and CO II polypeptides (SEQ ID NOs: 11 and 14), the following amino acid sequences were selected for PCR primers to amplify partial DNA sequences of CO I and CO II genes: SEQ ID NO: 9 and SEQ ID NO:10 for the CO I gene; and SEQ ID NO: 15 and SEQ ID NO:16 for the CO II gene. The third component (CO III), which was reported to be included in THE cytochrome c oxidase complex, did not exist in the preparation purified from *G. oxydans* DSM 4025. the absence OF CO III seemed to be due to the disassociation of the complex during purification. To confirm and amplify a partial DNA sequence encoding the assumed CO III gene of *G. oxydans* DSM 4025, if it in fact exists, two amino acid sequences corresponding to the conserved regions of the polypeptides encoded by the CO III genes of *P. denitrificans*,

*R. sphaeroides* and bovine mitochondria, were selected (FIG. 5.): SEQ ID NO: 17 and SEQ ID NO: 18 for the CO III gene. Each pair of primers was specifically designed for CO I, CO II or CO III (FIG. 6). The PCR reaction was carried out by using the GeneAmp™ DNA Amplification Reagent Kit (Takara Shuzo, Kyoto, Japan) with the Perkin-Elmer Cetus Instruments Thermal Cycler according to the recommendations of the supplier. The reaction consisted of 30 cycles of 1) a denaturation step at 94° C. for 1 minute; 2) an annealing step at 42 or 50° C. for 2 minutes; and 3) a synthesis step at 72° C. for 3 minutes. The reaction mixture (100 microliter) contained 200 micromole of dNTPs, 2.9 micromole (for 32 degeneracy) or 5.8 micromole (for 64 degeneracy) of each primer, 2.2 ng of chromosomal DNA of *G. oxydans* DSM 4025, and 2.5 units of Taq polymerase in the buffer supplied. PCR product was detected by agarose gel electrophoresis (AGE) with ethidium bromide staining. As a result, DNA fragments of expected length (about 180 bp for CO I, about 180 bp for CO II, about 300 bp for CO III) were amplified.

(2) Cloning and Nucleotide Sequencing of the DNA Fragments Amplified by PCR.

The PCR-amplified DNA fragments were purified from an agarose gel and directly cloned into the pCRTMII vector (Invitrogen Corporation, USA), and the DNA sequences were determined according to the supplier's instruction. Amino acid sequences deduced from the nucleotide sequences of the PCR products displayed considerable homology with the sequences of target positions in the sequence alignments (FIGS. 3 to 5). The PCR products encoding the partial amino acid sequences of CO I, CO II and CO III were labeled with $^{32}P$ to obtain probes Pco1, Pco2, and Pco3, respectively. The probes were used for Southern- or colony-hybridization to detect the complete CO I, CO II and CO III genes.

(3) Southern-Blot Analysis of the *G. oxydans* DSM 4025 Chromosomal DNA Using the PCR Products as Probes.

The chromosomal DNA of *G. oxydans* DSM 4025 digested with various restriction endonucleases was subjected to Southern hybridization using the probes. The probe Pco1 hybridized to a Pst I fragment (8.0 kb), and the probes Pco2 and Pco3 hybridized to an EcoRI fragment (9.3 kb), of the chromosomal DNA.

(4) Cloning of Complete Cytochrome c Oxidase Genes in the 8.0 kb PstI Fragment (CO I) and the 9.3 kb EcoRI Fragment (CO II and CO III).

The chromosomal DNA of *G. oxydans* DSM 4025 was completely digested with PstI or EcoRI and the resulting fragments were subjected to agarose gel electrophoresis. EcoRI-digests around 9.3 kb (7-12 kb) in size and PstI-digests around 8 kb (6-10 kb) were cut out and eluted from the gel. The recovered DNA fragments were ligated with PstI- or EcoRI-digested pUC19 vector to transform *E. coli* JM109. About 1,000 transformants were obtained as a PstI- or EcoRI-library. Colony hybridization was performed with the probe Pco1 on the PstI library and with the primers Pco2 and Pco3 on the EcoRI library. From each library, several positive colonies were obtained. Plasmid DNAs were extracted from the colonies and digested with PstI or EcoRI; an 8.0 kb PstI fragment showed a strong signal with the probe Pco1, and a 9.3 kb EcoRI fragment showed a strong signal with both of the probes Pco2 and Pco3. The plasmid containing 8.0 kb PstI fragment was designated as pUCO01 and the plasmid containing the 9.3 kb EcoRI fragment as pUCO23.

(5) Physical Map of the 8.0 kb PstI and 9.3 kb EcoRI Fragments.

Physical maps of the 8.0 kb PstI and 9.3 kb EcoRI fragments were constructed by Southern hybridization analysis of the fragments digested with various restriction endonucleases with the probes Pco1, Pco2 and Pco3. Direction and distance of the CO II and CO III genes encoded on the 9.3 kb EcoRI fragment were determined by the PCR method with primers derived from the partial nucleotide sequences (FIG. 7).

(6) Nucleotide Sequencing of the Complete CO I Gene.

The nucleotide sequence of the COI gene on pUCO01 was determined by the dideoxy chain termination method. A 2.9 kb fragment upstream from a HindIII site, as shown in FIG. 7, was sequenced and one open reading frame (CDS of 1,674 bp existing in the sequence shown in SEQ ID NO: 1) was found in the fragment. This ORF encodes a protein of 558 amino acids (sequence list SEQ ID NO: 2), containing the amino acid stretch consistent with the amino acid sequence (SEQ ID NO: 11) of the peptide fragment derived from the purified CO I and the amino acid sequence (SEQ ID NO: 13) deduced from the DNA sequence of the about –180 bp PCR product (SEQ ID NO: 12) for CO I (see 3-(1)). The CO I amino acid sequence of *G. oxydans* DSM 4025 displayed 78.7, 76.0 and 53.3% homology with those of *R. sphaeroides*, *P. denitrificans* and bovine mitochondria, respectively. (FIG. 8)

(7) Construction of an Expression Plasmid Encoding All of the CO I, CO II, and CO III Genes.

The CO I gene was isolated from the 8.0 kb PstI fragment on pUCO01 by complete HindIII- and partial-EcoRI digestion, as a 3.5 kb fragment (FIG. 7). According to the physical map of the 9.3 kb EcoRI fragment on pUCO23, the CO II and CO III genes were isolated by complete-KpnI and partial-PstI digestions yielding a 6.0 kb fragment in tandem form (FIG. 7). Each fragment was independently subcloned into the BluescriptII SK+ vector to obtain plasmids pBCO01 with a 3.5 kb fragment containing the CO I gene, and pBCO23 with a 6.0 kb fragment containing the CO II and CO III genes.

Figure 9:
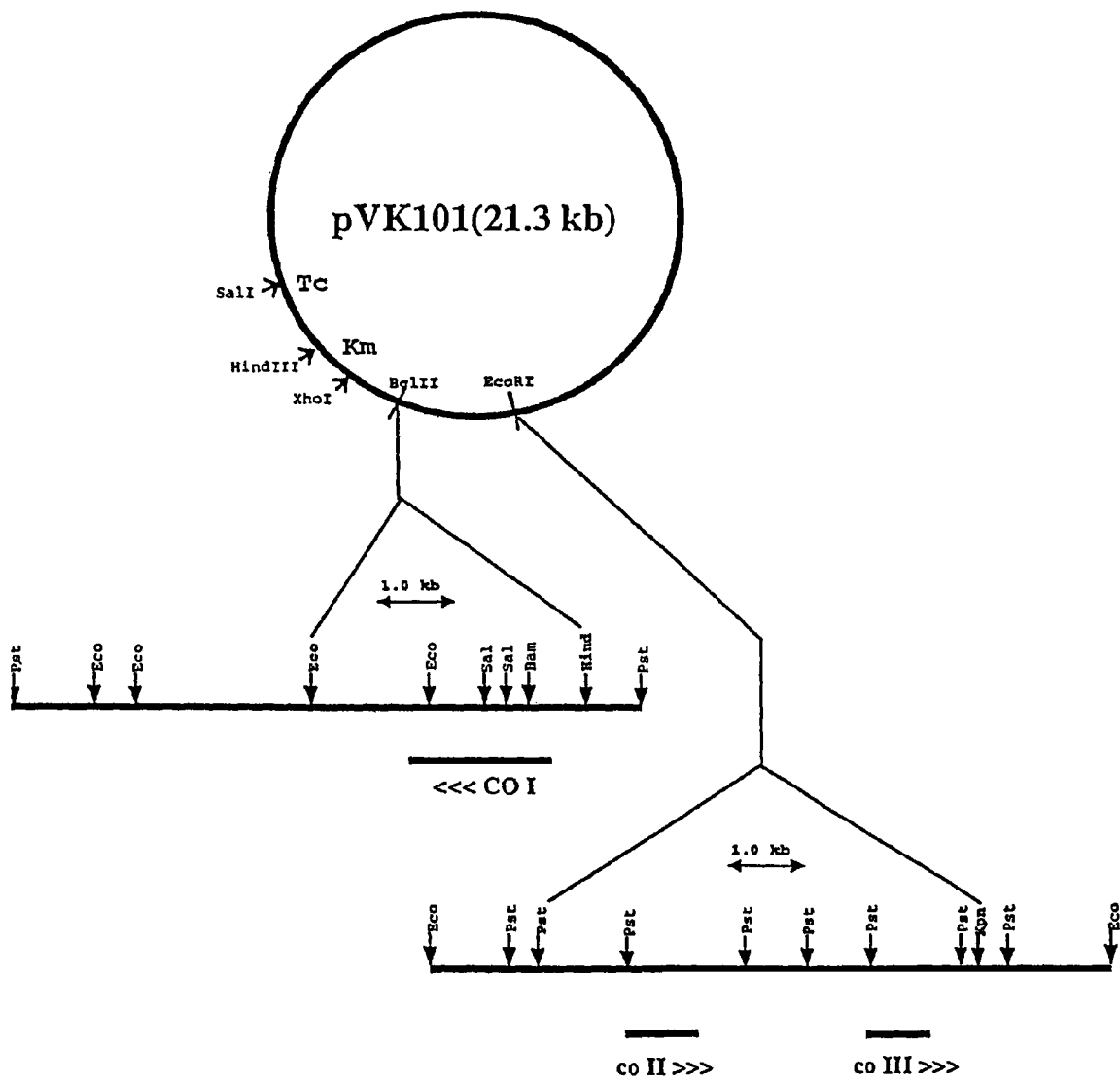
FIG. 9 shows a genetic map of the pVKcoxes construct used for expressing the genes of cytochrome c oxidase complex of *G. oxydans* DSM 4025.

As shown in FIG. 9, the 3.5 kb fragment containing the CO I gene and the 6.0 kb fragment containing the CO II and CO III genes were co-integrated in one expression vector for the functional expression of the genes of the cytochrome c oxidase complex (CO I, CO II, and CO III). First, the 6.0 kb XbaI-KpnI fragment the containing CO II and CO III genes from pBCO23 was inserted in the EcoRI site of the plasmid vector, pVK101 by blunt end ligation. Then, the 3.5 kb XbaI-HindIII fragment containing the CO I gene from pBCO01 was inserted in the BglII site of the pVK101 vector that already contained the 6.0 kb XbaI-KpnI fragment. The resulting plasmid vector was designated as pVKcoxes.

Example 4

Overexpression of Cytochrome c Oxidase Genes in a IDSM 4025 Derivative

The plasmid carrying the cytochrome c oxidase genes in pVK101, pVKcoxes, was introduced into a rifampicin resistant derivative of *G. oxydans* DSM 4025, GOS2 RPM (a single colony isolate from GOS2R; T. Hoshino et al., European Patent Publication 832974 A2) by the tri-parental conjugal mating method. Cells of GOS2 RPM were cultivated at 30° C. in 10 ml of T medium consisting of 3% Trypticase Soy Broth (Becton Dickinson, Cockeysville, Md., USA) and 0.3% yeast extract (Difco Laboratories, Detroit, Mich.) with 100 microgram/ml of rifampicin (TR medium). A donor strain, *E. coli* HB carrying pVKcoxes (Tc$^r$, Km$^r$) or pVK102

(Tc$^r$, Km$^r$) and a helper strain, *E. coli* HB101 carrying pRK2013 (Km$^r$) were grown in Luria Bertani medium containing appropriate antibiotics overnight at 37° C. These overnight cultures (10 ml of GOS2 RPM culture and 2 ml of *E. coli* culture) were independently centrifuged and cell pellets were independently suspended in 2 ml of T medium. One hundred microliter of the cell suspensions were mixed and 50 microliter of the mixed cell suspension was spotted onto a nitrocellulose filter placed on the surface of NS2 agar medium consisting of 5.0% D-mannitol, 0.25% $MgSO_4 \cdot 7H_2O$, 1.75% corn steep liquor, 5% baker's yeast (Oriental Yeast Co., Tokyo, Japan), 0.5% $CaCO_3$, 0.5% urea (separately sterilized), and 2.0% agar, pH 7.0 (before sterilization). The plate was incubated at 27° C. overnight. The resulting cells were spread onto T agar medium containing 100 microgram/ml rifampicin and 3 microgram/ml tetracycline (TRT agar plate). The transconjugants thus obtained were purified by streaking on TRT agar plates to remove cells of *E. coli* and plasmid-free GOS2 RPM.

The resulting transconjugants, GOS2 RPM (pVKcoxes) and GOS2R (pVK102) were cultivated, and cells of both transconjugants were prepared according to the method described in Example 1. The cytochrome c oxidase levels in GOS2 RPM (pVKcoxes) and GOS2 RPM (pVK102) were determined by the following experiments and compared with each other. From both strains, solubilized membrane fractions were prepared by the method described in Example 1. First, a-type heme contents were determined to be 0.031 and 0.022 nmoles/mg of cell proteins for GOS2 RPM (pVKcoxes) and GOS2R (pVK102), respectively, by the reduced minus oxidized difference spectrum method (Example 1). Second, the specific oxidation rate of cytochrome c (purchased from Sigma, horse heart type VI) was measured. Reduced cytochrome c was prepared by using sodium dithinite as a reducer, with excess reducer removed by two treatments with a PD-10 column (Pharmacia). The reaction mixture consisted of 33 mM reduced cytochrome c, 25 mM Na-HEPES (pH 7.2), 2% sucrose monolaurate and 0.5 mM EDTA. The oxidation rate of the reduced cytochrome c was measured as a decrease in absorbance at 550 nm with the molar coefficient taken as 21.1/mM/cm. Specific oxidation rates on the reduced cytochrome c were determined to be 1.58 and 2.00 nmoles/mg cell proteins/min for GOS2 RPM (pVK102) and GOS2R (pVKcoxes), respectively. Third, the amounts of CO I and CO II components were compared by Western-blot analysis with antibodies against the CO I or CO II components. Stronger band intensities (60% increase for CO I and 41% increase for CO II as measured with a CCD camera) were observed on GOS2 RPM (pVKcoxes). These results suggested that introduction of pVKcoxes resulted in functional amplification of the cytochrome c oxidase complex level in the 2KGA producing *G. oxydans* DSM 4025 derivative.

The invention being thus described, it will be obvious that the same may be varied in many ways. Such variations are not to be regarded as a departure from the spirit and scope of the invention and all such modifications are intended to be included within the scope of the following claims.

---

What is claimed is:

1. A process for producing 2-keto-L-gluconic acid (2-KGA) from L-sorbose or D-sorbitol comprising:
   (a) cultivating, in a culture medium, a recombinant *Gluconobacter oxydans* host cell comprising the polynucleotide of SEQ ID NO: 1 or a polynucleotide that encodes the polypeptide of SEQ ID NO: 2; and
   (b) recovering 2-KGA from the culture medium.

2. The process according to claim 1, wherein the host cell has the identifying characteristics of *Gluconobacter oxydans* DSM 4025.

3. The process according to claim 1, wherein the host cell is *Gluconobacter oxydans* DSM 4025.

4. A process for producing L-ascorbic acid from L-sorbose or D-sorbitol comprising:
   (a) producing 2-KGA by cultivating in a culture medium a recombinant *Gluconobacter oxydans* host cell comprising the polynucleotide of SEQ ID NO: 1 or a polynucleotide that encodes the polypeptide of SEQ ID NO: 2;
   (b) converting the 2-KGA into L-ascorbic acid; and
   (c) recovering L-ascorbic acid from the culture medium.

5. The process according to claim 4, wherein the host cell has the identifying characteristics of *Gluconobacter oxydans* DSM 4025.

6. The process according to claim 4, wherein the host cell is *Gluconobacter oxydans* DSM 4025.

7. The process according to claim 1, wherein the host cell is rifampycin-resistant.

8. The process according to claim 6, wherein the host cell is rifampycin-resistant.

* * * * *